(12) United States Patent
Wu et al.

(10) Patent No.: US 6,417,189 B1
(45) Date of Patent: Jul. 9, 2002

(54) AZA COMPOUNDS, PHARMACEUTICAL COMPOSITIONS AND METHODS OF USE

(75) Inventors: Yong-Qian Wu, Columbia; Wei Huang, Wildwood; Gregory S. Hamilton, Catonsville, all of MD (US)

(73) Assignee: GPI NIL Holdings, Inc., Wilmington, DE (US)

( * ) Notice: Subject to any disclaimer, the term of this patent is extended or adjusted under 35 U.S.C. 154(b) by 0 days.

(21) Appl. No.: 09/551,618

(22) Filed: Apr. 17, 2000

Related U.S. Application Data

(60) Provisional application No. 60/164,950, filed on Nov. 12, 1999.

(51) Int. Cl.[7] .................. A61K 31/495; C07D 243/00; C07D 401/00; C07D 231/02

(52) U.S. Cl. ............................ 514/252.01; 514/252.02; 514/252.03; 514/252.04; 514/252.05; 514/252.06; 514/218; 514/406; 514/407; 540/553; 544/238; 548/356.1; 548/364.1; 548/364.2; 548/364.3; 548/364.4; 548/364.5; 548/364.6; 548/364.7

(58) Field of Search ................... 514/252.01, 252.02, 514/252.03, 252.04, 252.05, 252.06, 218, 406, 407; 544/238; 540/553; 548/356.1, 364.1, 364.2, 364.3, 364.4, 364.5, 364.6, 364.7

(56) References Cited

U.S. PATENT DOCUMENTS

| | | | |
|---|---|---|---|
| 3,706,743 A | 12/1972 | Moon | 260/250 |
| 4,399,136 A | 8/1983 | Hassall et al. | 424/250 |
| 4,431,644 A | 2/1984 | Smith et al. | 424/246 |
| 4,561,880 A | 12/1985 | Shimano et al. | 71/92 |
| 4,581,220 A | 4/1986 | Nelson et al. | 423/658.5 |
| 4,593,094 A | 6/1986 | Nagano et al. | 544/224 |
| 4,659,711 A | 4/1987 | Huang et al. | 514/247 |
| 4,743,687 A | 5/1988 | Lawton et al. | 540/487 |
| 4,766,110 A | 8/1988 | Ryan el al. | 514/19 |
| 5,002,962 A | 3/1991 | Loscalzo | 514/410 |
| 5,002,964 A | 3/1991 | Loscalzo | 514/423 |
| 5,034,051 A | 7/1991 | Kume et al. | 544/1 |

(List continued on next page.)

FOREIGN PATENT DOCUMENTS

| | | |
|---|---|---|
| DE | 3636278 | 10/1986 |
| DE | 197 42 263 | 9/1997 |
| EP | 405994 | 1/1991 |
| EP | 443983 | 8/1991 |
| EP | 476933 | 3/1992 |
| EP | 488 258 | 6/1992 |
| EP | 805 147 | 11/1997 |
| WO | WO 88/09789 | 12/1988 |
| WO | WO 92/00278 | 1/1992 |
| WO | WO 92/04370 | 3/1992 |
| WO | WO 92/11245 | 7/1992 |
| WO | WO 92/11850 | 7/1992 |
| WO | WO 92/19593 | 11/1992 |
| WO | WO 92/21313 | 12/1992 |
| WO | WO 93/13066 | 7/1993 |
| WO | WO 93/14072 | 7/1993 |
| WO | WO 94/12474 | 6/1994 |
| WO | WO 94/15900 | 7/1994 |
| WO | WO 95/35308 | 12/1995 |
| WO | Wo 95/35367 | 12/1995 |
| WO | WO 96/06846 | 3/1996 |
| WO | WO 96/20725 | 11/1996 |
| WO | WO 96/20949 | 11/1996 |
| WO | WO 96/40140 | 12/1996 |
| WO | WO 96/40633 | 12/1996 |
| WO | WO 96/41609 | 12/1996 |
| WO | WO 97/23202 | 3/1997 |
| WO | WO 97/23458 | 3/1997 |
| WO | WO 97/36869 | 9/1997 |
| WO | WO 97/38008 | 10/1997 |

(List continued on next page.)

OTHER PUBLICATIONS

US 5,654,332, 08/1997, Armistead (withdrawn)

Gudasheva, T.A. et al., "Synthesis and antiamnesic activity of a series of N–acylprolyl–containing dipeptides," *Eur. J. Med. Chem.*, 1996, 31, 151–157.

Dawson, T. et al., "Immunosuppressant FK506 enhances phosphorylation of nitric oxide synthase and protects against glutamate neurotoxicity," *Proc. Natl. Acad. Sci. USA*, 1993, 90, 9808–9812.

Dawson, T. et al., "The immunophilins, FK506 binding protein and cyclophilin, are discretely localized in the brain: relationship to calcineurin," *Neuroscience*, 1994, 62, 569–580.

Gold, B. et al., "Regulation of the Transcription Factor c–JUN by nerve growth factor in adult sensory neurons," *Neuroscience Letters*, 1993, 154, 129–133.

Gold, B. et al., "Regulation of aberrant neurofilament phosphorylation in neuronal perikarya. IV. Evidence for the involvement of two signals," *Brain Research*, 1993, 626, 23–30.

Gold, B. et al., "The immunosuppressant FK506 increases functional recovery and nerve regeneration following peripheral nerve injury," *Restorative Neurology and Neuroscience*, 1994, 6, 287–296.

Gold, B. et al., "Multiple signals underlie the axotomy–induced up–regulation of c–JUN in adult sensory neurons," *Neuroscience Letters*, 1994, 176, 123–127.

Gold, B. et al., "The immunosuppressant FK506 increases the rate of axonal regeneration in rat sciatic nerves," *J. Neuroscience*, 1995, 15, 7509–7516.

Hamilton, G. et al., "Neuroimmunophilin Ligands as Novel Therapeutics for the Treatment of Degenerative Disorders of the Nervous System," p. 1–71.

(List continued on next page.)

*Primary Examiner*—Richard L. Raymond
*Assistant Examiner*—Tamthom N. Truong
(74) *Attorney, Agent, or Firm*—Lyon & Lyon LLP

(57) ABSTRACT

The present invention relates to N-substituted cyclic aza compounds, pharmaceutical compositions comprising such compounds, and methods of their use for effecting neuronal activities.

27 Claims, No Drawings

U.S. PATENT DOCUMENTS

| | | |
|---|---|---|
| 5,128,483 A | 7/1992 | Trybulski .................. 548/531 |
| 5,149,872 A | 9/1992 | Messina et al. ............. 564/151 |
| 5,166,317 A | 11/1992 | Wallace et al. ............. 530/350 |
| 5,192,773 A | 3/1993 | Armistead et al. .......... 514/315 |
| 5,214,034 A | 5/1993 | Nakayama et al. ......... 514/159 |
| 5,215,969 A | 6/1993 | Springer et al. .............. 514/21 |
| 5,232,923 A | 8/1993 | Fukazawa et al. ........ 514/237.5 |
| 5,310,738 A | 5/1994 | Nakayama .................. 544/224 |
| 5,321,009 A | 6/1994 | Baeder et al. .................. 514/4 |
| 5,330,993 A | 7/1994 | Armistead et al. .......... 514/330 |
| 5,342,942 A | 8/1994 | Jaen et al. .................. 544/250 |
| 5,359,138 A | 10/1994 | Takeuchi et al. ............ 562/567 |
| 5,453,437 A | 9/1995 | Schohe et al. .............. 514/424 |
| 5,504,197 A | 4/1996 | Schubert et al. ........... 536/23.5 |
| 5,506,243 A | 4/1996 | Ando et al. ................. 514/345 |
| 5,516,797 A | 5/1996 | Armistead et al. .......... 514/548 |
| 5,527,907 A | 6/1996 | Or et al. ..................... 540/456 |
| 5,536,737 A | 7/1996 | Kobayashi et al. ......... 514/365 |
| 5,541,189 A | 7/1996 | Luly et al. .................. 514/291 |
| 5,543,423 A | 8/1996 | Zelle et al. ................. 514/332 |
| 5,614,547 A | 3/1997 | Hamilton et al. ........... 514/423 |
| 5,620,971 A | 4/1997 | Armistead et al. .......... 514/212 |
| 5,629,325 A | 5/1997 | Lin et al. .................... 514/318 |
| 5,643,908 A | 7/1997 | Sugimara et al. ........... 514/247 |
| 5,665,774 A | 9/1997 | Armistead et al. .......... 514/533 |
| 5,684,151 A | 11/1997 | Combs ....................... 544/224 |
| 5,696,135 A | 12/1997 | Steiner et al. ............... 514/317 |
| 5,703,088 A | 12/1997 | Sharpe et al. ............... 514/278 |
| 5,714,485 A | 2/1998 | Lumma et al. .............. 514/247 |
| 5,714,510 A | 2/1998 | Proctor ....................... 514/423 |
| 5,717,092 A | 2/1998 | Armistead et al. .......... 544/129 |
| 5,721,256 A | 2/1998 | Hamilton et al. ........... 514/330 |
| 5,744,485 A | 4/1998 | Zelle et al. ................. 514/318 |
| 5,750,690 A | 5/1998 | Broger et al. ............... 544/234 |
| 5,780,484 A | 7/1998 | Zelle et al. ................. 514/316 |
| 5,786,378 A | 7/1998 | Hamilton et al. ........... 514/423 |
| 5,795,908 A | 8/1998 | Hamilton et al. ........... 514/423 |
| 5,798,355 A | 8/1998 | Steiner et al. ............... 514/248 |
| 5,801,187 A | 9/1998 | Li et al. ...................... 514/365 |
| 5,801,197 A | 9/1998 | Steiner et al. ............... 514/548 |
| 5,811,434 A | 9/1998 | Zelle .......................... 514/307 |
| 5,840,736 A | 11/1998 | Zelle .......................... 514/332 |
| 5,843,960 A | 12/1998 | Steiner et al. ............... 514/317 |
| 5,846,979 A | 12/1998 | Hamilton et al. ........... 514/311 |
| 5,846,981 A | 12/1998 | Steiner et al. ............... 514/317 |
| 5,859,031 A | 1/1999 | Hamilton et al. ........... 514/343 |
| 5,874,449 A | 2/1999 | Hamilton et al. ........... 514/330 |
| 5,898,029 A | 4/1999 | Lyons et al. .................. 514/12 |
| 5,935,989 A | 8/1999 | Hamilton et al. ........... 514/423 |
| 5,958,949 A | 9/1999 | Hamilton et al. ........... 514/318 |
| 5,968,957 A | 10/1999 | Hamilton et al. ........... 514/330 |
| 5,990,131 A | 11/1999 | Hamilton et al. ........... 514/330 |
| 6,022,878 A | 2/2000 | Steiner et al. ............... 514/317 |
| 6,037,370 A | 3/2000 | Armistead .................. 514/533 |
| 6,054,452 A | 4/2000 | Hamilton et al. ........... 514/212 |

FOREIGN PATENT DOCUMENTS

| | | |
|---|---|---|
| WO | WO 97/20554 | 12/1997 |
| WO | WO 97/48681 | 12/1997 |
| WO | WO 97/49695 | 12/1997 |
| WO | WO 98/13343 | 2/1998 |
| WO | WO 98/08814 | 3/1998 |
| WO | WO 98/08827 | 3/1998 |
| WO | WO 98/37885 | 3/1998 |
| WO | WO 98/20891 | 5/1998 |
| WO | WO 98/20892 | 5/1998 |
| WO | WO 98/20893 | 5/1998 |
| WO | WO 98/29117 | 9/1998 |
| WO | WO 98/55091 | 10/1998 |
| WO | WO 98/24805 | 11/1998 |
| WO | WO 99/10340 | 3/1999 |

OTHER PUBLICATIONS

Kitamura et al., "Suppressive Effect of FK–506, a Novel Immunosuppressant, Against MPTP–Induced Dopamine Depletion in the Striatum of Young C57BL/6 Mice," *J. Neuroimmunology*, 1994, 50, 221–224.

Lyons, W. E. et al., "Immunosuppressant FK506 promotes neurite outgrowth in cultures of PC 12 cells and sensory ganglia," *Proc. Natl. Acad. Sci. USA*, 1994, 91, 3191–3195.

Lyons, W. E. et al., "Neuronal Regeneration Enhances the Expression of the Immunophilin FKBP–12," *J. Neuroscience*, 1995, 15(4), 2985–2994.

Ryba et al., "Cyclosporine A Prevents Neurological Deterioration of Patients with SAH—A Preliminary Report," *Acta Neurochirurgica*, 1991, 112, 25–27.

Shiga et al., "Cyclosporin A Protects Against Ischemia–Reperfusion Injury in the Brain," *Brain Research*, 1992, 595, 145–148.

Snyder, S. et al., "Immunophilins and the Nervous System", *Nature Medicine*, 1995, 1, 32–37.

Steiner, J. et al., "High brain densities of the immunophilin FKBP colocalized with calcineurin," *Nature*, 1992, 358, 584–587.

Steiner, J. et al., "Nonimmunosuppressive ligands for neuroimmunophilins promote nerve extension in vitro and in vivo," *Society for Neuroscience Abstracts*, 1996, 22, 297.13.

Steiner, J. et al., "Neurotrophic immunophilin ligands stimulate structural and functional recovery in neurodegenerative animal models," *Proc. Natl. Acad. Sci. USA*, 1997, 94, 2019–2024.

Steiner, J. et al., "Neurotrophic actions of nonimmunosuppressive analogues of immunosuppressive drugs FK506, rapamycin and cyclosporin A," *Nature Medicine*, 1997, 421–428.

Teichner et al., "Treatment with Cyclosporine A Promotes Axonal Regeneration in Rats Submitted to Transverse Section of the Spinal Cord," *Int'l. J. Brain Research & Neurobio.*, 1993, 34(3), 343–349.

Kozikowski, A.P. et al., "Alzheimer's Therapy: An Approach to Novel Muscarinic Ligands Based Upon the Naturally Occurring Alkaloid Himbacine," *Bioorg. & Med. Chem. Lett.*, 1992, 2, 797–802.

Nicolaides, E.D. et al., "Modified Di– and Tripeptides of the C–Terminal Portion of Oxytocin and Vasopressin as Possible Cognition Activation Agents," *J. Med. Chem.*, 1986, 29, 959–971.

DeRuiter, Jack et al., "In Vitro Aldose Reductase Inhibitory Activity of Substituted N–Benzenesulfonyl–glycine Derivatives," *J. Pharm. Sci.*, 1987, 76(2), 149–152.

Caufield, C. et al., "Macrocyclic Immunomodulators," *Ann. Rep. Med. Chem.*, 1989, 195–204.

Zouikri, Chemical Abstracts, vol. 129:216907, 1998.
Didierjean, Chemical Abstracts, vol. 128:137758, 1997.
Senoo, Chemical Abstracts, vol. 125:295188, 1996.
Bock, Chemical Abstracts, vol. 123:340467, 1995.
Kao, Chemical Abstracts, vol. 123:83100, 1995.
Didierjean, Chemical Abstracts, vol. 124:146778, 1995.
Pinnen, Chemical Abstracts, vol. 121:701283, 1994.
Casini, Chemical Abstracts, vol. 120:270095, 1993.
Brunner, Chemical Abstracts, vol. 119:95312, 1993.
Lecoq, Chemical Abstracts, vol. 119:181221, 1993.
Bock, Chemical Abstracts, vol. 117:111477, 1992.

Hosodo, Chemical Abstracts, vol. 118:255342, 1992.
Pissiotas, Chemical Abstracts, vol. 116:214522, 1992.
Lecoq, Chemical Abstracts, vol. 118:39364, 1992.
Sato, Chemical Abstracts, vol. 117:145248, 1992.
Kume, Chemical Abstracts, vol. 91:106452, 1991.
Onodera, Chemical Abstracts, vol. 116:20783, 1991.
Kume, Chemical Abstracts, vol. 113:211999, 1990.
Kume, Chemical Abstracts, vol. 90:13073, 1990.
Henke, Chemical Abstracts, vol. 112:179895, 1989.
Kume, Chemical Abstracts, vol. 110:173245, 1988.
Hagiwara, Chemical Abstracts, vol. 109:110447, 1988.
Haga, Chemical Abstracts, vol. 108:94578, 1987.
Haga, Chemical Abstracts, vol. 105:20519, 1986.
Nagano, Chemical Abstracts, vol. 86:63224, 1986.
Haga, Chemical Abstracts, vol. 86:60572, 1986.

Nagano, Chemical Abstracts, vol. 86:32884, 1986.
Sumitomo, Chemical Abstracts, vol. 102:132057, 1984.
Kobayashi, Chemical Abstracts, vol. 101:191944, 1984.
Nagano, Chemical Abstracts, vol. 84:31794, 1984.
Nagano, Chemical Abstracts, vol. 99:194984, 1983.
Kornet, Chemical Abstracts, vol. 95:62107, 1981.
Dutta, Chemical Abstracts, vol. 89:191427, 1978.
Wakabayashi, Chemical Abstracts, vol. 88:50904, 1977.
Wakabayashi, Chemical Abstracts, vol. 86:29859, 1976.
Wakabayashi, Chemical Abstracts, vol. 85:473445, 1976.
Dutta, Chemical Abstracts, vol. 83:193683, 1975.
Zinner, Chemical Abstracts, vol. 58:4577c, 1962.
Luttringhaus, Chemical Abstracts, vol. 54:4606h, 1959.
Rink, Chemical Abstracts, vol. 54:560d, 1959.

ABZA COMPOUNDS, PHARMACEUTICAL COMPOSITIONS AND METHODS OF USE

This application claims the benefit of U.S. Provisional Application No. 60/164,950 filed Nov. 12, 1999.

BACKGROUND OF THE INVENTION

The present invention relates to N-substituted cyclic aza compounds, pharmaceutical compositions comprising such compounds, and methods of their use for effecting neuronal activities.

DESCRIPTION OF RELATED ART

Neuroimmunophilins

The peptidyl-prolyl isomerases ("PPIases") are a family of ubiquitous enzymes which catalyze the interconversion of cis and trans amide bond rotamers adjacent to proline residues in peptide substrates. See, for example, Galat, A., Eur. J. Biochem. (1993) 216:689–707 and Kay, J. E., Biochem. J. (1996) 314:361–385. The PPIases have been referred to as "immunophilins" because of their interaction with certain immunosuppressant drugs. Schreiber, S. L., Science (1991) 251:283–287; Rosen, M. K. and Schreiber, S. L., Angew. Chem. Intl. Ed. Engi. (1992) 31:384–400.

The PPIase, cyclophilin A, was found to be the intracellular protein target for the potent immunosuppressant drug cyclosporin A. Subsequently, the structurally unrelated macrolide immunosuppressant FK506 was discovered to bind to a different PPIase enzyme which was named FK506-binding protein, or FKBP. Rapamycin, another macrolide drug which is a structural analogue of FK506, also interacts with FKBP.

All three of these drugs bind to their respective immunophilins and inhibit the respective PPIase activities. However, inhibition of immunophilin enzymatic activity is not the cause of the observed immunosuppressive effects. Binding of the drugs to the immunophilins results in the formation of "activated complexes", which interact with downstream proteins to inhibit proliferation of T-lymphocytes. Schreiber, supra; Rosen, et al., supra. In the case of FK506, binding to FKBP results in a drug-protein complex which is a potent inhibitor of the calcium-calmodulin-dependent protein phosphatase, calcineurin. Bierer, B. E., Mattila, P. S., Standaert, R. F., Herzenberg, L. A., Burakoff, S. J., Crabtree, G., Schreiber, S. L., Proc. Natl. Acad. Sci. USA (1990) 87:9231–9235; Liu, J., Farmer, J. D., Lane, W. S., Friedman, J., Weissman, I., Schreiber, S. L.; Cell (1991) 66:807–815.

Neither FK506 or FKBP alone appreciably inhibits calcineurin's activity. Inhibiting calcineurin blocks the signaling pathway by which the activated T-cell receptor causes transcription of the gene for interleukin-2, inhibiting the immune response. Despite the structural dissimilarity between FK506 and cyclosporin A (and cyclophilin and FKBP), the cyclosporin A-cyclophilin complex also inhibits calcineurin, and thus cyclosporn A and FK506 have the same mechanism of action.

On the other hand, while rapamycin and FK506 have similar structures and bind to the same immunophilin (FKBP), rapamycin's mechanism of action is different from that of FK506. The complex of FKBP12 with rapamycin interacts with a protein called FPAP, or RAFT, and in so doing blocks the signal pathway leading from the IL-2 receptor on the surface of T-cells to promotion of entry into the cell cycle in the nucleus. Sabatini, D. M., Erdjument-Bromage, H., Lui, M.; Tempst, P., Snyder, S. H., Cell (1994) 78:35–43; Brown, E. J., Albers, M. W., Shin, T. B., Ichikawa, K., Keith, C. T., Lane, W. S., Schreiber, S. L. Nature (1994) 369:756–758; Brown, E. J., Beal, P. A., Keith, C. T., Chen, J., Shin, T. B., Schreiber, S. L., Nature (1995) 377:441–446.

Thus, all three drugs produce the same effect—suppression of T-cell proliferation—but do so by inhibiting distinct signal transduction pathways. The introduction of cyclosporin("CsA") marked a breakthrough in organ transplantation, and the drug became a major pharmaceutical product. The subsequent discovery of rapamycin ("Rapamycin") and FK506 further fueled interest in the cellular basis of the actions of these drugs. The discovery of the interaction of the immunophilins with CsA, FK506 and Rapamycin led to research on the mechanistic basis of immunophilin-mediated immunosuppression.

Immunophilins and the Nervous System

Because the initial interest in the immunophilins was largely driven by their role in the mechanism of action of the immunosuppressant drugs, most of the original studies of these proteins and their actions focused on the tissues of the immune system. In 1992, it was reported that levels of FKBP12 in the brain were 30 to 50 times higher than in the immune tissues. Steiner, J. P., Dawson, T. M., Fotuhi, M., Glatt, C. E., Snowman, A. M., Cohen, N., Snyder, S. H., Nature (1992) 358:584–587. This finding suggested a role for the immunophilins in the functioning of the nervous system. Both FKBP and cyclophilin were widely distributed in the brain and were found almost exclusively within neurons. The distribution of the immunophilins in the brain closely resembled that of calcineurin, suggesting a potential neurological link. Steiner, J. P., Dawson, T. M., Fotuhi, M., Glatt, C. E., Snowman, A. M., Cohen, N., Snyder, S. H., Nature (1992) 358:584–587; Dawson, T. M., Steiner, J. P., Lyons, W. E., Fotuhi, M., Blue, M., Snyder, S. H., Neuroscience (1994) 62: 569–580.

Subsequent work demonstrated that the phosphorylation levels of several known calcineurin substrates were altered in the presence of FK506. Steiner, J. P., Dawson, T. M., Fotuhi, M., Glatt, C. E., Snowman, A. M., Cohen, N., Snyder, S. H., Nature (1992) 358:584–587. One of the proteins affected by FK506 treatment, GAP-43, mediates neuronal process elongation. Lyons, W.E., Steiner, J. P., Snyder, S. H., Dawson, T. M., J. Neurosci. (1995) 15:2985–2994. This research revealed that FKBP12 and GAP-43 were upregulated in damaged facial or sciatic nerves in rats. Also, FKBP12 was found in very high levels in the growth cones of neonatal neurons. FK506 was tested to determine whether or not it might have an effect on nerve growth or regeneration. In cell culture experiments with PC12 cells or sensory neurons from dorsal root ganglia, FK506 promoted process (neurite) extension with subnanomolar potency. Lyons, W. E., George, E. B., Dawson, T. M., Steiner, J. P., Snyder, S. H., Proc. Nati. Acad. Sci. USA (1994) 91:3191–3195. Gold et al. demonstrated that FK506 functioned as a neurotrophic agent in vivo. In rats with crushed sciatic nerves, FK506 accelerated nerve regeneration and functional recovery. Gold, B.G., Storm-Dickerson, T., Austin, D. R. , Restorative Neurol. Neurosci., (1994) 6:287; Gold, B. G., Katoh, K., Storm-Dickerson, T. J, Neurosci. (1995) 15:7509–7516. See, also, Snyder, S. H., Sabatini, D. M., Nature Medicine (1995) 1:32–37 (regeneration of lesioned facial nerves in rats augmented by FK506).

Besides FK506, rapamycin and cyclosporin also produced potent neurotrophic effects in vitro in PC12 cells and chick sensory neurons. Steiner, J. P., Connolly, M. A., Valentine, H. L., Hamilton, G. S., Dawson, T. M., Hester, L., Snyder, S. H., *Nature Medicine* (1997) 3:421–428. As noted above, the mechanism for immunosuppression by rapamycin is different than that of FK506 or cyclosporin. The observation that rapamycin exerted neurotrophic effects similar to FK506 and cyclosporin suggested that the nerve regenerative effects of the compounds are mediated by a different mechanism than that by which they suppress T-cell proliferation.

Analogues of FK506, rapamycin, and cyclosporin which bind to their respective immunophilins, but are devoid of immunosuppressive activity, are known in the art. Thus, the FK506 analogue L-685,818 binds to FKBP but does not interact with calcineurin, and is therefore nonimmunosuppressive. Dumont, F. J., Staruch, M. J., Koprak, S. L., *J. Exp. Med.* (1992) 176:751–760.

Similarly, 6-methyl-alanyl cyclosporin A (6-[Me]-ala-CsA) binds to cyclophilin but likewise lacks the ability to inhibit calcineurin. The rapamycin analogue WAY-124,466 binds FKBP but does not interact with RAFT, and is likewise nonimmunosuppressive. Ocain, T. D., Longhi, D., Steffan, R. J., Caccese, R. G., Sehgal, S. N., *Biochem. Biophys. Res. Commun.* (1993) 192:1340–1346; Sigal, N. H., Dumont, F., Durette, P., Siekierka, J. J., Peterson, L., Rich, D., *J. Exp. Med.* (1991) 173:619–628. These nonimmunosuppressive compounds were shown to be potent neurotrophic agents in vitro, and one compound, L-685,818, was as effective as FK506 in promoting morphological and functional recovery following sciatic nerve crush in rats. Steiner, J. P., Connolly, M. A., Valentine, H. L., Hamilton, G. S., Dawson, T. M., Hester, L., Snyder, S. H., *Nature Medicine* (1997) 3:421–428. These results demonstrated that the neurotrophic properties of the immunosuppressant drugs could be functionally dissected from their immune system effects.

Published work by researchers studying the mechanism of action of FK506 and similar drugs had shown that the minimal FKBP-binding domain of FK506 (as formulated by Holt et al., *Bio Med. Chem. Lett.* (1994) 4:315–320) possessed good affinity for FKBP. Hamilton et al. proposed that the neurotrophic effects of FK506 resided within the immunophilin binding domain, and synthesized a series of compounds which were shown to be highly effective in promoting neurite outgrowth from sensory neurons, often at picomolar concentrations. Hamilton, G. S., Huang, W., Connolly, M. A., Ross, D. T., Guo, H., Valentine, H. L., Suzdak, P. D., Steiner, J. P., *Bio Med. Chem. Lett.* (1997). These compounds were shown to be effective in animal models of neurodegenerative disease.

FKBP12 Inhibitors/Ligands

A number of researchers in the early 1990s explored the mechanism of immunosuppression by FK506, cyclosporin and rapamycin, and sought to design second-generation immunosuppressant agents that lacked the toxic side effects of the original drugs. A pivotal compound, 506BD (for "FK506 binding domain" see Bierer, B. E., Somers, P. K., Wandless, T-J., Burakoff, S. J., Schreiber, S. L., *Science* (1990) 250:556–559), retained the portion of FK506 which binds FKBP12 in an intact form, while the portion of the macrocyclic ring of FK506 which extends beyond FKBP12 in the drug-protein complex was significantly altered. The finding that 506BD was a high-affinity ligand for, and inhibitor of, FK506, but did not suppress T-cell proliferation was the first demonstration that the immunosuppressant effects of FK506 were not simply caused by rotamase activity inhibition.

In addition to various macrocyclic analogues of FKS506 and rapamycin, simplified compounds which represent the excised FKBP binding domain of these drugs were synthesized and evaluated. Non-macrocyclic compounds with the FKBP-binding domain of FK506 excised possess lower affinity for FKBP12 than the parent compounds. Such structures still possess nanomolar affinity for the protein. See, e.g., Hamilton, G. S., Steiner, J. P., *Curr. Pharm. Design* (1997) 3:405–428; Teague, S. J., Stocks, M. J., *Bio Med. Chem. Lett.*, (1993) 3:1947–1950; Teague, S. J., Cooper, M. E., Donald, D. K., Furber, M., *Bio Med. Chem. Lett.* (1994) 4:1581–1584.

Holt et al. published several studies of simple pipecolate FKBP12 inhibitors which possessed excellent affinity for FKBP12. In initial studies, replacement of the pyranose ring of FK506 mimetics demonstrated that simple alkyl groups such as cyclohexyl and dimethylpentyl worked well in this regard. Holt et al., *Bio Med. Chem. Lett.* (1994) 4:315–320. Simple compounds possessed good affinity for FKBP12 ($K_i$ values of 250 and 25 nM, respectively). These structures demonstrated that these simple mimics of the binding domain of FKB506 bound to the immunophilin in a manner nearly identical to that of the corresponding portion of FK506. Holt, D. A., Luengo, J. I., Yamashita, D. S., Oh, H. J., Konialian, A. L., Yen, H. K., Rozamus, L. W., Brandt, M., Bossard, M. J., Levy, M. A., Eggleston, D. S., Liang, J., Schultz, L. W.; Stout, T. J.; Clardy, I., *J. Am. Chem. Soc.* (1993) 115:9925–9938.

Armistead et al. also described several pipecolate FKBP12 inhibitors. X-ray structures of the complexes of these molecules with FKBP also demonstrated that the binding modes of these simple structures were related to that of FK506. Armistead, D. M., Badia, M. C., Deininger, D. D., Duffy, J. P., Saunders, J. O., Tung, R. D., Thomson, J. A.; DeCenzo, M. T.; Futer, O., Livingston, D. J., Murcko, M. A., Yamashita, M. M., Navia, M. A., *Acta Cryst.* (1995) D51:522–528.

As expected from the noted effector-domain model, FKBP12 ligands lacking an effector element were inactive as immunosuppressant agents, failing to suppress lymphocyte proliferation both in vitro and in vivo.

Neuroorotective/Neuroreaenerative Effects of FKBP12 Ligands

Steiner et al., U.S. Pat. No. 5,696,135 (issued Dec. 9, 1997) describe the neurotrophic actions of a large number of compounds such as those described above. Cultured chick sensory neurons were used as an in vitro assay to measure the ability of compounds to promote neurite outgrowth (fiber extension) in neurons Componds were also tested for their ability to bind to FBP12 and inhibit its enzymatic (rotamase) activity. As the data demonstrate, many of these compounds were found to be extremely potent nerve growth agents, promoting fiber extension from cultured neurons with half-maximal effects seen in some cases,at picomolar concentrations. The effects of these simple FKBP12 ligands on nervous tissue are comparable to, or in some cases more potent than, FK506 itself.

Some of the compounds were also shown to promote regrowth of damaged peripheral nerves in vivo. Steiner, J. P., Connolly, M. A., Valentine, H. L., Hamilton, G. S., Dawson, T. M., Hester, L., Snyder, S. H., *Nature Medicine* (1997) 3:421–428. In whole-animal experiments in which the sciatic nerves of rats were crushed with forceps and animals treated with these compounds subcutaneously, there was found significant regeneration of damaged nerves relative to control animals, resulting in both more axons in drug-treated animals and axons with a greater degree of myelination. Lesioning of the animals treated only with vehicle caused a significant decrease in axon number (50% decrease compared to controls) and degree of myelination (90% decrease compared to controls). Treatment with the FKBP12 ligands resulted in reduction in the decrease of axon number (25% and 5% reduction, respectively, compared to controls) and in the reduction of myelination levels (65% and 50% decrease compared to controls). Similar results were subsequently reported by Gold et al Gold, B. G., Zeleney-Pooley, M., Wang, M. S., Chaturvedi, P.; Armistead, D. M., *Exp. Neurobiol.* (1997) 147:269–278.

Several of these compounds were shown to promote recovery of lesioned central dopaminergic neurons in an animal model of Parkinson's Disease. Hamilton, G. S., Huang, W., Connolly, M. A., Ross, D. T., Guo, H., Valentine, H. L., Suzdak, P. D., Steiner, J. P., *Bio Med. Chem. Lett.* (1997). N-Methyl-4-phenyl-1,2,3,6-tetrahydropyridine ("MPTP") is a neurotoxin which selectively destroys dopaminergic neurons. Gerlach, M., Riederer, P., Przuntek, H., Youdim, M. B., *Eur. J. Pharmacol.* (1991) 208:273–286. The nigral-striatal dopaminergic pathway in the brain is responsible for controlling motor movements.

Parkinson's Disease is a serious neurodegenerative disorder resulting from degeneration of this motor pathway. Lesioning of the nigral-striatal pathway in animals with MPTP has been utilized as an animal model of Parkinson's Disease. In mice treated with MPTP and vehicle, a substantial loss of 60–70% of functional dopaminergic terminals was observed as compared to non-lesioned animals. Lesioned animals receiving FKBP12 ligands concurrently with MPTP showed a striking recovery of TH-stained striatal dopaminergic terminals, as compared with controls, suggesting that FKBP12 ligands may possess potent neuroprotective and neuro-regenerative effects on both peripheral as well as central neurons.

Other compounds which have an affinity for FKBP12 may also possess neurotrophic activities similar to those described above. For example, one skilled in the art is referred to the following patents and patent applications for their teaching of neurotrophic compounds which are lacking immunosuppressive activity:

Hamilton et al., U.S. Pat. No. 5,614,547 (Mar. 25, 1997);
Steiner et al., U.S. Pat. No. 5,696,135 (Dec. 9, 1997);
Hamilton et al., U.S. Pat. No. 5,721,256 (Feb. 24, 1998);
Hamilton et al., U.S. Pat. No. 5,786,378 (Jul. 28, 1998);
Hamilton et al., U.S. Pat. No. 5,795,908 (Aug. 18, 1998);
Steiner et al., U.S. Pat. No. 5,798,355 (Aug. 25, 1998);
Steiner et al., U.S. Pat. No. 5,801,197 (Sep. 1, 1998);
Li et al., U.S. Pat. No. 5,801,187 (Sep. 1, 1998); and
Hamilton et al., U.S. Pat. No. 5,935,989 (Aug. 10, 1999).

These molecules are effective ligands for, and inhibitors of, FKBP12 and are also potent neurotrophic agents in vitro, promoting neurite outgrowth from cultured sensory neurons at naromolar or subnanolar dosages.

Additionally, as noted, compounds which possess immunosuppressive activity, for example, FK506, CsA and Rapamycin, among others, also may possess a significant level of neurotrophic activity. Thus, to the extent that such compounds additionally may possess activities, including neurotrophic activities, such compounds are intended to be included within the term "sensorineurotrophic compound" as used herein. The following publications provide disclosures of compounds which presumably possess immunosuppressive activities, as well as possibly other activities, and are likewise intended to be included within the term "sensorineurotrophic compound" as used herein:

Armistead et al., U.S. Pat. No. 5,192,773 (Mar. 9, 1993);
Armistead et al., U.S. Pat. No. 5,330,993 (Jul. 19, 1994);
Armistead et al., U.S. Pat. No. 5,516,797 (May 14, 1996);
Armistead et al., U.S. Pat. No. 5,620,971 (Apr. 15, 1997);
Armistead et al., U.S. Pat. No. 5,622,970 (Apr. 22, 1997);
Armistead et al., U.S. Pat. No. 5,665,774 (Sep. 9, 1997); and
Zelle et al., U.S. Pat. No. 5,780,484 (Jul. 14, 1998).

The neuroregenerative and neuroprotective effects of FKBP12 ligands are not limited to dopaminergic neurons in the central nervous system. In rats treated with para-chloroamphetamine ("PCA"), an agent which destroys neurons which release serotonin as a neurotransmitter, treatment with an FKBP ligand was reported to exert a protective effect. Steiner, J. P., Hamilton, G. S., Ross, D. T., Valentine, H. L., Guo, H., Connolly, M. A., Liang, S., Ramsey, C., Li, J.H., Huang, W., Howorth, P.; Soni, R., Fuller, M., Sauer, H., Nowotnick, A., Suzdak, P. D., *Proc. Natl. Acad. Sci. USA* (1997) 94:2019–2024. In rats lesioned with PCA, cortical density of serotonin fibers was reduced 90% relative to controls. Animals receiving the ligand showed a greater serotonin innervation in the cortex serotonergic innervation in the somatosensory cortex was increased more than two-fold relative to lesioned, non-drug treated animals.

Similarly, such ligands have been shown to induce sprouting of residual cholinergic axons following partial transection of the fimbria fornix in rats. Guo, H., Spicer, D. M., Howorth, P., Hamilton, G. S., Suzdak, P. D, Ross, D. T., *Soc. Neurosci. Abstr.* (1997) 677.12. The transection produced a 75–80% deafferentiation of the hippocampus. Subcutaneous administration of the FBKP12 ligand produced a four-fold sprouting of spared residual processes in the CA1, CA3 and dentate gyrus regions of the hippocampus, resulting in significant recovery of cholinergic innervation in all three regions as quantitated by choline acetyltransferase (ChAT) density.

Taken together, the data in the noted references indicate that certain ligands for FKBP12, preferably those which are non-immunosuppressive, comprise a class of potent active neurotrophic compounds which have been referred to as "neuroimmunophilins" or "neuroimmunophilin ligands" with potential for therapeutic utility in the treatment or prevention of neurodegenerative diseases. Thus, in the context of the present invention, a sensorineurotrophic compound is meant to encompass those compounds which have been designated as neuroimmunophilins and which also may have, but are not required to have, binding affinity for an FKBP. The ultimate mechanism of action and whether or not such compounds also possess other activity such as, for example, immunosuppressive activity, is not determinative of whether the compound is neurotrophic, promotes hair growth, regenerates vision, or improves memory for purposes of the invention, as long as the compound in question is possesses the desired effect on nerve cells, hair follicles, eye tissues, or brain cells.

Until the present invention, none of the prior work disclosed the use of the inventive compounds in effecting neuronal activity, including stimulation of damaged neurons, promotion of neuronal regeneration, prevention of neurodegeneration and treatment of neurological disorder.

Neurological Disorders

It has been found that picomolar concentrations of an immunosuppressant such as FK506 and rapamycin stimulate neurite outgrowth in PC12 cells and sensory nervous, namely dorsal root ganglion cells (DRGs). Lyons et al., supra In whole animal experiments, FK506 has been shown to stimulate nerve regeneration following facial nerve injury and results in functional recovery in animals with sciatic nerve lesions.

Several neurotrophic factors effecting specific neuronal populations in the central nervous system have been identified. For example, it has been hypothesized that Alzheimer's disease results from a decrease or loss of nerve growth factor (NGF). It has thus been proposed to treat Alzheimer's patients with exogenous nerve growth factor or other neurotrophic proteins such as brain derived nerve factor (BDNF), glial derived nerve factor, ciliary neurotrophic factor, and neurotropin-3 to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressants exhibit a number of potentially serious side effects including nephrotoxicity, such as impairment of glomerular filtration and irreversible interstitial fibrosis (Kopp et al., 1991, *J. Am. Soc. Nephrol.* 1:162); neurological deficits, such as involuntary tremors, or non-specific cerebral angina such as non-localized headaches (De Groen et al., 1987, *N. Engl. J. Med.* 317:861); and vascular hypertension with complications resulting therefrom (Kahan et al., 1989 *N. Engl. J. Med.* 321: 1725).

Accordingly, there is a need for compounds for treating neurological disorders.

SUMMARY OF THE INVENTION

The present invention relates to N-substituted cyclic aza compounds. Preferred compounds include N-glyoxyl cyclic aza derivative compounds, N-sulfonyl cyclic aza derivative compounds, tertiary N-aminocarbonyl cyclic aza compounds, and secondary N-aminocarbonyl cyclic aza compounds.

The present invention further relates to pharmaceutical compositions comprising such compounds in combination with a pharmaceutically acceptable carrier.

The present invention also relates to methods of using such compounds to effect neuronal activity.

DETAILED DESCRIPTION OF THE INVENTION

Definitions

"Alkyl" refers to a branched or unbranched saturated hydrocarbon chain comprising a designated number of carbon atoms. For example, $C_1$–$C_9$ alkyl is a straight or branched hydrocarbon chain containing 1 to 9 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" refers to a branched or unbranched unsaturated hydrocarbon chain comprising a designated number of carbon atoms. For example, $C_2$–$C_9$ alkenyl is a straight or branched hydrocarbon chain containing 2 to 9 carbon atoms having at least one double bond, and includes but is not limited to substituents such as ethenyl, propenyl, iso-propenyl, butenyl, iso-butenyl, tert-butenyl, n-pentenyl, n-hexenyl, and the like, unless otherwise indicated.

"Alkoxy" refers to the group -OR wherein R is alkyl as herein defined. Preferably, R is a branched or unbranched saturated hydrocarbon chain containing 1 to 9 carbon atoms.

"Aryl" refers to an aromatic, hydrocarbon cyclic moiety having one or more closed rings. Examples include, without limitation, phenyl, naphthyl, anthracenyl, phenanthracenyl, biphenyl and pyrenyl.

"Heteroaryl" refers to an aromatic, cyclic moiety having one or more closed rings with one or more heteroatoms (for example, sulfur, nitrogen or oxygen) in at least one of the rings. Examples include, without limitation, pyrrole, thiophene, pyridine and isoxazole.

"Carbocycle" refers to a hydrocarbon, cyclic moiety having one or more closed rings that is/are alicyclic, aromatic, fused and/or bridged. Examples include cyclopropanyl, cyclobutyl, cyclopentane, cyclohexane, cycloheptane, cyclooctane, cyclopentene, cyclohexene, cycloheptene, cycloctene, benzene, naphthalene, anthracene, phenanthracene, biphenyl and pyrene.

"Heterocycle" refers to a cyclic moiety having one or more closed rings that is/are alicyclic, aromatic, fused and/or bridged, with one or more heteroatoms (for example, sulfur, nitrogen or oxygen) in at least one of the rings. Examples include, without limitation, pyrrolidine, pyrrole, thiazole, thiophene, piperidine, pyridine, isoxazolidine and isoxazole.

"Derivative" refers to a substance produced from another substance either directly or by modification or partial substitution.

"Effective amount" refers to the amount required to produce the desired effect. "Therapeutically effective amount" refers to the amount required to effect a neuronal activity.

"Halo" refers to at least one fluoro, chloro, bromo or iodo moiety. "Isosteres" refer to elements, molecules, or ions having different molecular formulae but exhibiting similar or identical physical properties. For example, tetrazole is an isostere of carboxylic acid because it mimics the properties of carboxylic acid even though they both have very different molecular formulae. Typically, two isosteric molecules have similar or identical volumes and shapes. Ideally, isosteric compounds should be isomorphic and able to co-crystallize. Among the other physical properties that isosteric compounds usually share are boiling point, density, viscosity and thermal conductivity. However, certain properties are usually different: dipolar moments, polarity, polarization, size and shape since the external orbitals may be hybridized differently. The term "lisosteres" encompass "bioisosteres".

"Bioisosteres" are isosteres which, in addition to their physical similarities, share some common biological properties. Typically, bioisosteres interact with the same recognition site or produce broadly similar biological effects.

"Carboxylic acid isosteres" include without limitation direct derivatives such as hydroxamic acids, acylcyanamides and acylsulfonamides; planar acidic heterocycles such as tetrazoles, mercaptoazoles, sulfinylazoles, sulfonylazoles, isoxazoles, isothiazoles, hydroxythiadiazoles and hydroxychromes; and nonplanar sulfur- or phosphorus-derived acidic functions such as phosphinates, phosphonates, phosphonamides, sulphonates, sulphonamides, and acylsulphonamides. Examples include, without limitation, —COOH, —COSR$_3$, —CSSR$_3$, —CSOR$_3$, —SO$_3$H, —SO$_2$HNR$_3$, —CN, —PO$_2$(R$_3$)$_2$, —PO$_3$(R$_3$)$_2$, —OR$_3$, —SR$_3$, —NHCOR$_3$, —N(R$_3$)$_2$, —CON(R$_3$)$_2$, —CSN(R$_3$)$_2$, —CONH(O)R$_3$, —CONHNHSO$_2$R$_3$, —COHNSO$_2$R$_3$, —CONR$_3$CN, or any of the following structures:

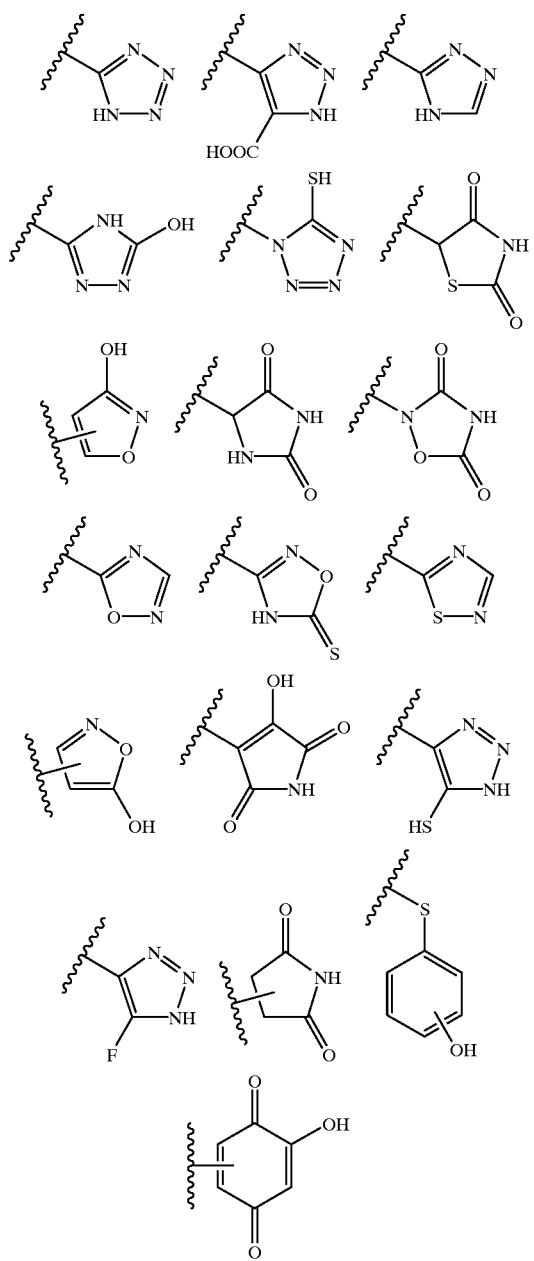

wherein any of said ring structures may be optionally substituted at one or more position(s) with one or more substituent(s).

"Low molecular weight, small molecule compounds" include, without limitation, molecules which are smaller in size, molecular weight, or both in relation to the compounds Rapamycin, Cyclosporin, and FK506 Preferably, such compounds have a molecular weight no more than about 800 daltons; more preferably, no more than about 650 daltons; and most preferably, no more than about 500 daltons.

"Pharmaceutically acceptable carrier" refers to any carrier, diluent, excipient, suspending agent, lubricating agent, adjuvant, vehicle, delivery system, emulsifier, disintegrant, absorbent, preservative, surfactant, colorant, flavorant, or sweetener. For these purposes, the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal, and intracranial injection or infusion techniques.

"Pharmaceutically acceptable salt" refers to a salt of the inventive compounds which possesses the desired pharmacological activity and which is neither biologically nor otherwise undesirable. The salt can be formed with inorganic acids such as acetate, adipate, alginate, aspartate, benzoate, benzenesulfonate, bisulfate butyrate, citrate, camphorate, camphorsulfonate, cyclopentapronionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. The basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Enantiomers" refer to a pair of stereoisomers that are non-superimposable mirror images of each other.

"Isomers" refer to compounds having the same number and kind of atoms, and hence the same molecular weight, but differing in respect to the arrangement or configuration of the atoms.

"Optical isomers" refer to either of two kinds of stereoisomers. One kind is represented by mirror-image structures called enantiomers, which result from the presence of one or more asymmetric carbon atoms in the compound (glyceraldehyde, lactic acid, sugars, tartaric acid, amino acids). The other kind is exemplified by diastereoisomers, which are not mirror images. These occur in compounds having two or more asymmetric carbon atoms; thus, such compounds have $2_n$, optical isomers, where n is the number of asymmetric carbon atoms.

"Stereoisomers" refer to isomers that differ only in the arrangement of the atoms in space. "Diastereoisomers" are stereoisomers which are not mirror images of each other.

"Racemic mixture", refers to a mixture containing equal parts of individual enantiomers. "Non-racemic mixture" is a mixture containing unequal parts of individual enantiomers or stereoisomers.

"R" or "$R_m$", where m is an integer, designate various substituents. Each R group is independently selected at each instance it appears in a molecule. For example, "—$(R_3)_2$" denotes two $R_3$ substituents, wherein each of said $R_3$ substituents may differ from the other; thus, $R_3$ may be a branched alkyl in one instance, and an aryl substituted with one or more substituents in the second instance.

"Alopecia" refers to deficient hair growth and partial or complete loss of hair, including without limitation androgenic alopecia (male pattern baldness), toxic alopecia, alopecia senilis, alopecia areata, alopecia pelada and trichotillomania. Alopecia results when the pilar cycle is disturbed. The most frequent phenomenon is a shortening of the hair growth or anagen phase due to cessation of cell proliferation. This results in an early onset of the catagen phase, and consequently a large number of hairs in the telogen phase during which the follicles are detached from the dermal papillae, and the hairs fall out. Alopecia has a number of etiologies, including genetic factors, aging, local and systemic diseases, febrile conditions, mental stresses, hormonal problems, and secondary effects of drugs.

"Animal" refers to a living organism having sensation and the power of voluntary movement, and which requires for its existence oxygen and organic food. Examples include, without limitation, an animal such as a member of the human, equine, porcine, bovine, murine, canine, or feline species. A preferred animal is mammal. In the case of a human, an "animals" may also be referred to as a "patient".

"Disease" refers to any deviation from or interruption of the normal structure or function of any part, organ, or system (or combinations) of the body that is manifested by a characteristic set of symptoms and signs and whose etiology, pathology, and prognosis may be known or unknown. *Dorland's Illustrated Medical Dictionary*, (W. B. Saunders Co. 27th ed. 1988).

"Disorder" refers to any derangement or abnormality of function; a morbid physical or mental state. *Dorland's Illustrated Medical Dictionary*, (W. B. Saunders Co. 27th ed. 1988).

"Enhancing memory performance" refers to improving or increasing the mental faculty by which to register, retain or recall past experiences, knowledge, ideas, sensations, thoughts or impressions.

"Eye" refers to the anatomical structure responsible for vision in humans and other animals,. and encompasses the following anatomical structures, without limitation: lens, vitreous body, ciliary body, posterior chamber, anterior chamber, pupil, cornea, iris, canal of Schlemm, zonules of Zinn, limbus, conjunctiva, choroid, retina, central vessels of the retina, optic nerve, fovea centralis, macula lutea, and sclera.

"Memory impairment" refers to a diminished mental registration, retention or recall of past experiences, knowledge, ideas, sensations, thoughts or impressions. Memory impairment may affect short and long-term information retention, facility with spatial relationships, memory (rehearsal) strategies, and verbal retrieval and production. Common causes of memory impairment are age, severe head trauma, brain anoxia or ischemia, alcoholic-nutritional diseases, drug intoxications and neurodegenerative diseases. For example, memory impairment is a common feature of neurodegenerative diseases such as Alzheimer's disease and senile dementia of the Alzheimer type. Memory impairment also occurs with other kinds of dementia such as multi-infarct dementia, a senile dementia caused by cerebrovascular deficiency, and the Lewy-body variant of Alzheimer's disease with or without association with Parkinson's disease. Creutzfeldt-Jakob disease is a rare dementia with which memory impairment is associated. It is a spongiform encephalopathy caused by the prion protein; it may be transmitted from other sufferers or may arise from gene mutations. Loss of memory is also a common feature of brain-damaged patients. Brain damage may occur, for example, after a classical stroke or as a result of an anaesthetic accident, head trauma, hypoglycemia, carbon monoxide poisoning, lithium intoxication, vitamin ($B_1$, thiamine and $B_{12}$) deficiency, or excessive alcohol use. Korsakoff's amnesic psychosis is a rare disorder characterized by profound memory loss and confabulation, whereby the patient invents stories to conceal his or her memory loss. It is frequently associated with excessive alcohol intake. Memory impairment may furthermore be age-associated; the ability to recall information such as names, places and words seems to decrease with increasing age. Transient memory loss may also occur in patients, suffering from a major depressive disorder, after electro-convulsive therapy.

"Neopsic factors" refers to compounds useful in treating vision loss, preventing vision degeneration, or promoting vision regeneration.

"Neurotrophic" includes without limitation the ability to stimulate neuronal regeneration or growth, and/or the ability to prevent or treat neurodegeneration. Preferably, neurotrophic compounds exhibit an MPTP Assay value which is greater than about 20% recovery of TH-stained dopaminergic neurons; more preferably, greater than about 35% recovery of TH-stained dopaminergic neurons; most preferably, greater than about 50% recovery of TH-stained dopaminergic neurons.

"Non-immunosuppressive" refers to the inability of compounds to trigger an immune response when compared to a control such as FK506 or cyclosporin A. Assays for determining immunosuppression are well known to those of ordinary skill in the art. Specific, non-limiting examples of well known assays include PMA and OKT3 wherein mitogens are used to stimulate proliferation of human peripheral blood lymphocytes (PBC) and the compounds are evaluated on their ability to inhibit such proliferation.

"Ophthalmologic" or "ocular" refers to anything about or concerning the eye.

"Pilar cycle" refers to the life cycle of hair follicles, and includes three phases:

(1) the anagen phase, the period of active hair growth which, insofar as scalp hair is concerned, lasts about three to five years;

(2) the catagen phase, the period when growth stops and the follicle atrophies which, insofar as scalp hair is concerned, lasts about one to two weeks; and (3) the telogen phase, the rest period when hair progressively separates and finally falls out which, insofar as scalp hair is concerned, lasts about three to four months.

Normally 80 to 90 percent of the follicles are in the anagen phase, less than 1 percent being in the catagen phase, and the rest being in the telogen phase. In the telogen phase, hair is uniform in diameter with a slightly bulbous, non-pigmented root. By contrast, in the anagen phase, hair has a large colored bulb at its root.

"Promoting hair growth" refers to maintaining, inducing, stimulating, accelerating, or revitalizing the germination of hair.

"Promoting vision regeneration" refers to maintaining, improving, stimulating or accelerating recovery of, or revitalizing one or more components of the visual system in a manner which improves or enhances vision, either in the presence or absence of any ophthalmologic disorder, disease, or injury.

"Treatina" refers to:

(i) preventing a disease, disorder or condition from occurring in an animal which may be predisposed to the disease, disorder and/or condition but has not yet been diagnosed as having it;

(ii) inhibiting the disease, disorder or condition, i.e., arresting its development; and/or (iii) relieving the disease, disorder or condition, i.e., causing regression of the disease, disorder and/or condition.

"Treating alopecia" refers to:
(i) preventing alopecia in an animal which may be predisposed to alopecia; and/or
(ii) inhibiting, retarding or reducing alopecia; and/or
(iii) promoting hair growth; and/or
(iv) prolonging the anagen phase of the hair cycle; and/or
(v) converting vellus hair to growth as terminal hair. Terminal hair is coarse, pigmented, long hair in which the bulb of the hair follicle is seated deep in the dermis. Vellus hair, on the other hand, is fine, thin, non-pigmented short hair in which the hair bulb is located superficially in the dermis. As alopecia progresses, the hairs change from the terminal to the vellus type.

"Treating memory impairment" refers to:
(i) preventing memory impairment from occurring in an animal which may be predisposed to memory impairment but has not yet been diagnosed as having it;
(ii) inhibiting memory impairment, i.e., arresting its development;
(iii) relieving memory impairment, i.e., causing its regression; and/or
(iv) enhancing memory.

"Enhancing memory performance" refers to improving or increasing the mental faculty by which to register, retain or recall past experiences, knowledge, ideas, sensations, thoughts or impressions.

"Vision" refers to the ability of humans and other animals to process images.

"Vision disorder" refers to any disorder that affects or involves vision, including without limitation visual impairment, orbital disorders, disorders of the lacrimal apparatus, disorders of the eyelids, disorders of the conjunctiva, disorders of the cornea, cataracts, disorders of the uveal tract, disorders of the optic nerve or visual pathways, free radical induced eye disorders and diseases, immunologically-mediated eye disorders and diseases, eye injuries, and symptoms and complications of eye disease, eye disorder, or eye injury.

"Visual impairment" refers to any dysfunction in vision including, without limitation, disturbances or diminution in vision (e.g., binocular, central, peripheral, scotopic), visual acuity for objects near and for, visual field, ocular motility, color perception, adaptation to light and dark, accommodation, refraction, and lacrimation. *See Physicians' Desk Reference (PDR) for Ophthalmology*, 16th Edition, 6:47 (1988).

"Visual system" includes the eyes, the extraocular muscles which control eye position in the bony orbit (eye socket), the optic and other nerves that connect the eyes to the brain, and those areas of the brain that are in neural communication with the eyes.

Unless the context clearly dictates otherwise, the definitions of singular terms may be extrapolated to apply to their plural counterparts as they appear in the application; likewise, the definitions of plural terms may be extrapolated to apply to their singular counterparts as they appear in the application.

COMPOUNDS OF THE PRESENT INVENTION

The present invention relates to an N-substituted cyclic aza compound. The compound may be polycyclic. Preferably, the compound is low molecular weight, small molecule, neurotrophic and/or N,N'-disubstituted. In a particularly preferred embodiment, the compound is non-immunosuppressive, or otherwise does not exert any significant immunosuppressive activity. In another preferred embodiment, the compound has an affinity for (for example, binds to or otherwise interacts with) FKBP-type immunophilins, such as FKBP12; such binding or interaction may inhibit the prolyl-peptidyl cis-trans isomerase, or rotamase, activity of the binding protein.

In one embodiment, the compound is an N-glyoxyl cyclic aza derivative compound having an affinity for an FKBP-type immunophilin, or a pharmaceutically acceptable salt, ester or solvate thereof. Preferably, the N-glyoxyl cyclic aza derivative compound has a structure of formula I

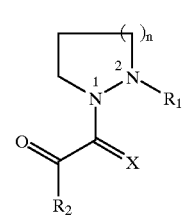

or a pharmaceutically acceptable salt, ester or solvate thereof, wherein:
n is 1–3;
$R_1$ is —$CR_3$, —$COOR_3$, —$COR_3$ or a carboxylic acid isostere, wherein said carboxylic acid isostere is unsubstituted or substituted with one or more substituent(s);
$R_2$ and $R_3$ are independently hydrogen, $C_1$–$C_9$ alkyl, $C_2$–$C_9$ alkenyl, aryl, heteroaryl, carbocycle or heterocycle, wherein said alkyl, alkenyl, aryl heteroaryl, carbocycle or heterocycle is unsubstituted or substituted with one or more substituent(s); and
X is O or S.
$R_3$ may differ at each instance it appears in a molecule.

In another embodiment, the compound is an N-sulfonyl cyclic aza derivative compound having an affinity for an FKBP-type immunophilin, or a pharmaceutically acceptable salt, ester or solvate thereof. Preferably, the compound has a structure of formula II

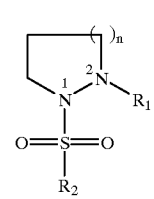

or a pharmaceutically acceptable salt, ester or solvate thereof, wherein:
n is 1–3;
$R_1$ is —$CR_3$, —$COOR_3$, —$COR_3$ or a carboxylic acid isostere, wherein said carboxylic acid isostere is unsubstituted or substituted with one or more substituent(s), wherein $R_1$ is preferably not —$CON(R_3)_2$; and
$R_2$ and $R_3$ are independently hydrogen, $C_1$–$C_9$ alkyl, $C_2$–$C_9$ alkenyl, aryl, heteroaryl, carbocycle or heterocycle, wherein said alkyl, alkenyl, aryl heteroaryl, carbocycle or heterocycle is unsubstituted or substituted with one or more substituent(s).

In a further embodiment, the compound is tertiary N-aminocarbonyl cyclic aza compound having an affinity for an FKBP-type immunophilin. Preferably, the tertiary N-aminocarbonyl cyclic aza compound has a structure of formula III

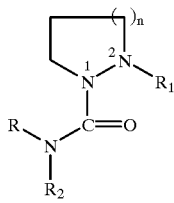

III or a pharmaceutically acceptable salt, ester or solvate thereof, wherein:
  n is 1–3;
  R$_1$ is —CR$_3$, —COOR$_3$, —COR$_3$ or a carboxylic acid isostere, wherein said carboxylic acid isostere is unsubstituent or substituted with one or more substituent(s);
  R and R$_2$ are independently C$_1$–C$_9$ alkyl, C$_2$–C$_9$ alkenyl, aryl, heteroaryl, carbocycle or heterocycle, wherein said alkyl, alkenyl, aryl heteroaryl, carbocycle or heterocycle is unsubstituted or substituted with one or more substituent(s); and
  R$_3$ is hydrogen C$_1$–C$_9$ alkyl, C$_2$–C$_9$ alkenyl, aryl, heteroaryl, carbocycle or heterocycle, wherein said alkyl, alkenyl, aryl heteroaryl, carbocycle or heterocycle is unsubstituted or substituted with one or more substituent (s)

In a final embodiment, the compound is a secondary N-aminocarbonyl cyclic aza compound having an affinity to FKBP-type immunophilins. Preferably, the secondary N-aminocarbonyl cyclic aza compound has a structure of formula IV

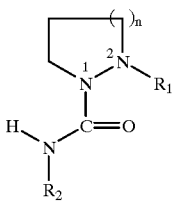

IV or a pharmaceutically acceptable salt, ester or solvate thereof, wherein:
  n is 1–3;
  R$_1$ is —CR$_3$, —COOR$_3$, —COR$_3$ or a carboxylic acid isostere, wherein said carboxylic acid isostere is unsubstituted or substituted with one or more substituent(s); and
  R$_2$ is C$_1$–C$_9$ alkyl, C$_2$–C$_9$ alkenyl, aryl, heteroaryl, carbocycle or heterocycle, wherein said alkyl, alkenyl, aryl heteroaryl, carbocycle or heterocycle is substituted with one or more substituent (s), wherein at least one of said substituent(s) is preferably —COOH; and
  R$_3$ is hydrogen, C$_1$–C$_9$ alkyl, C$_2$–C$_9$ alkenyl, aryl, heteroaryl, carbocycle or heterocycle, wherein said alkyl, alkenyl, aryl heteroaryl, carbocycle or heterocycle is unsubstituted or substituted with one or more substituent(s).

Preferably, the carboxylic acid isostere is —COOR, —COSR$_3$, —CSSR$_3$, —CSOR$_3$, —SO$_3$H, —SO$_2$HNR$_3$, —CN, —PO$_2$(R$_3$)$_2$, —PO$_3$(R$_3$)$_2$, —OR$_3$, —SR$_3$, —NHCOR$_3$, —N(R$_3$)$_2$, —CON(R$_3$)$_2$, —CSN(R$_3$)$_2$, CONH(O)R$_3$, —CONHNHSO$_2$R$_3$, —COHNSO$_2$R$_3$, —CONR$_3$CN, or any of the following structures:

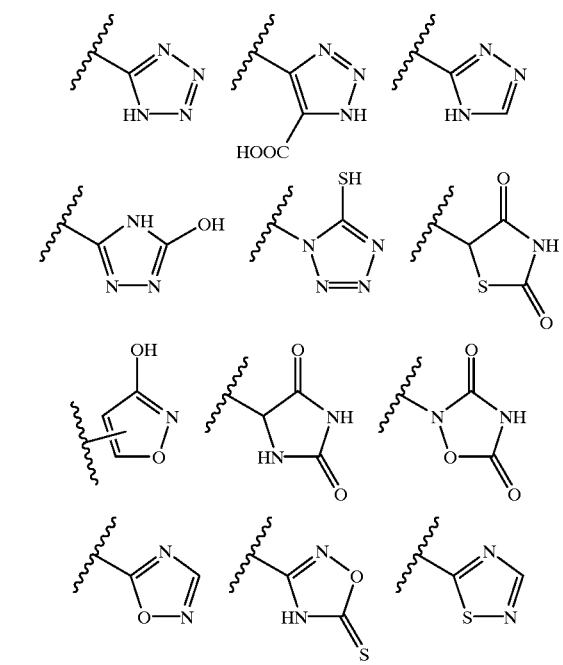

wherein any of said ring structures may be optionally substituted at one or more position(s) with one or more substituent(s).

Possible substituents of said alkyl, alkenyl, aryl, heteroaryl, carbocycle and heterocycle include, without limitation, C$_1$–C$_9$ straight or branched chain alkyl, C$_2$–C$_9$ straight or branched chain alkenyl, C$_1$–C$_9$ alkoxy, C$_2$–C$_9$ alkenyloxy, phenoxy, benzyloxy, C$_3$–C$_8$ cycloalkyl, C$_5$–C$_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties. Carbocyclic moieties include alicyclic and aromatic structures.

Examples of useful carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

Representative compounds of the present invention are set forth below.

| No. | Structure | Name |
|---|---|---|
| 1 | 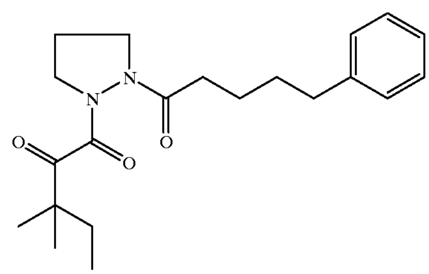 | 3,3-dimethyl-N-[2-(5-phenylpentanoyl)-tetrahydro-1H-1-pyrazolyl]-1,2-pentanedione |
| 2 | 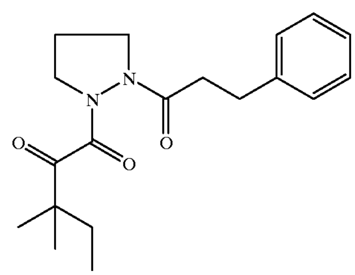 | 3,3-dimethyl-N-[2-(5-phenylpropanoyl)tetrahydro-1H-1-pyrazolyl]-1,2-pentanedione |
| 3 | 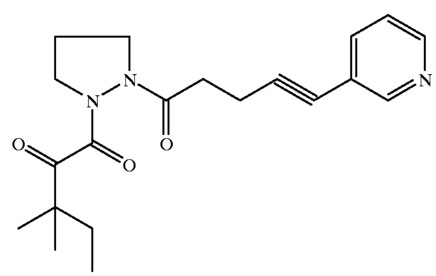 | 3,3-dimethyl-1-[2-(5-(3-pyridyl)pent-4-ynoyl)-pyrazolidinyl]-pentane-1,2-dione |
| 4 | 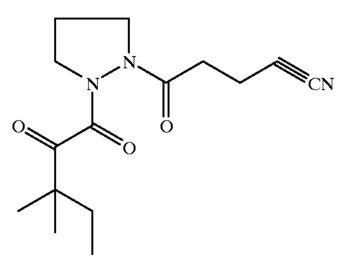 | 3,3-dimethyl-1-(2-pent-4-ynoylpyrazolidinyl)-pentane-1,2-dione |

-continued

| No. | Structure | Name |
|---|---|---|
| 5 | 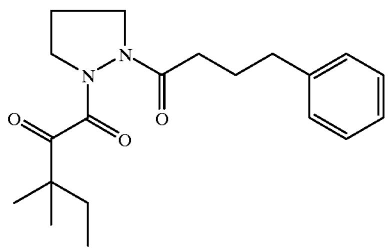 | 3,3-dimethyl-1-[2-(4-phenylbutanoyl)-pyrazolidinyl]pentane-1,2-dione |
| 6 | 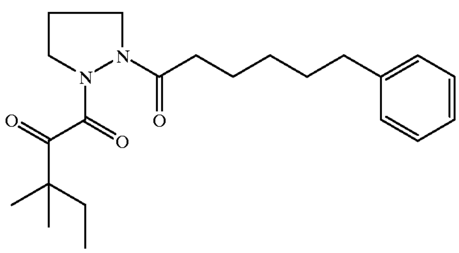 | 3,3-dimethyl-1-(2-(6-phenylhexanoyl)-pyrazolidinyl]pentane-1,2-dione |
| 7 | 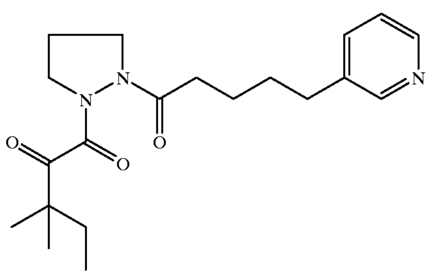 | 3,3-dimethyl-1-[2-(5-(3-pyridyl)pentanoyl)-pyrazolidinyl]pentane-1,2-dione |
| 8 | 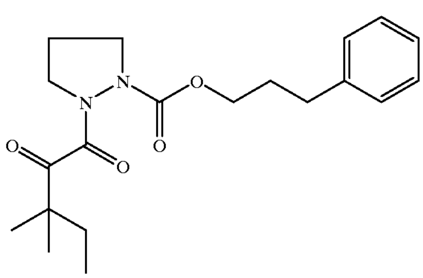 | 3-phenylpropyl 2-(3,3-dimethyl-2-oxopentanoyl)-pyrazolidinecarboxylate |
| 9 | 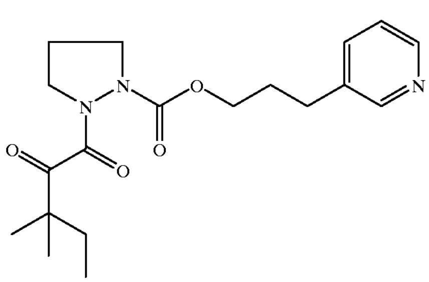 | 3-(3-pyridyl)propyl 2-(3,3-dimethyl-2-oxopentanoyl)-pyrazolidinecarboxylate |

-continued

| No. | Structure | Name |
|---|---|---|
| 10 | 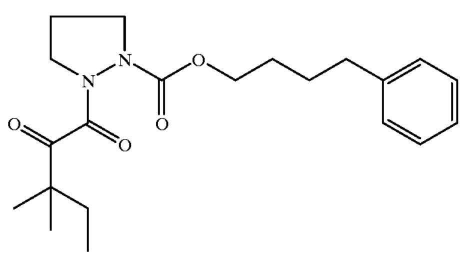 | 4-phenylbutyl 2-(3,3-dimethyl-2-oxopentanoyl)-pyrazolidinecarboxylate |
| 11 | 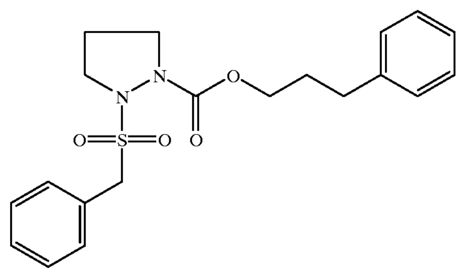 | 3-phenylpropyl 2-[benzylsulfonyl]-pyrazolidine-carboxylate |
| 12 | 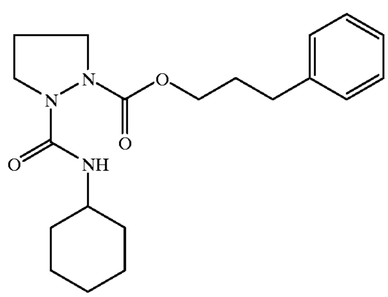 | 3-phenylpropyl 2-(N-cyclohexylcarbamoyl)-pyrazolidine-carboxylate |
| 13 | 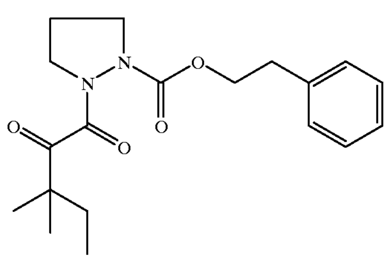 | 2-phenylethyl 2-(3,3-dimethyl-2-oxopentanoyl)-pyrazolidinecarboxylate |
| 14 | 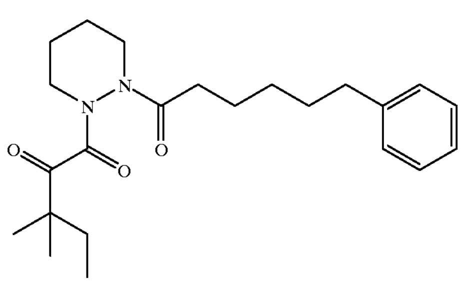 | 3,3-dimethyl-1-[2-(6-phenylhexanoyl)-perhydropyridazinyl]-pentane-1,2-dione |

-continued

| No. | Structure | Name |
|---|---|---|
| 15 | 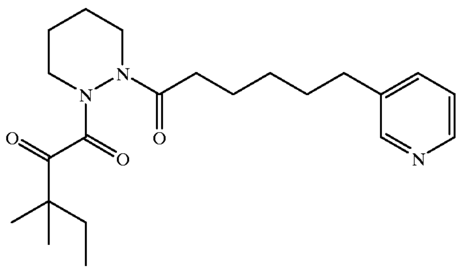 | 3,3-dimethyl-1-[2-(6-(3-pyridyl)hexanoyl)-perhydropyridazinyl]-pentane-1,2-dione |
| 16 | 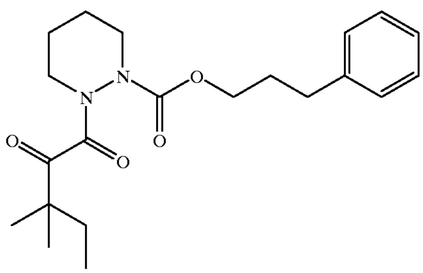 | 3-phenylpropyl 2-(3,3-dimethyl-2-oxopentanoyl)-perhydropyridazine-carboxylate |
| 17 | 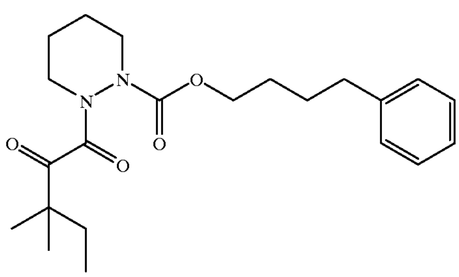 | 4-phenylbutyl 2-(3,3-dimethyl-2-oxopentanoyl)perhydro-pyridazinecarboxylate |
| 18 | 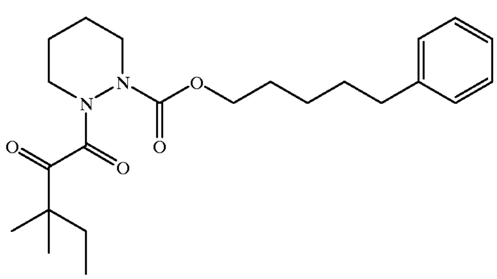 | 5-phenylpentyl 2-(3,3-dimethyl-2-oxopentanoyl)perhydro-pyridazinecarboxylate |
| 19 | 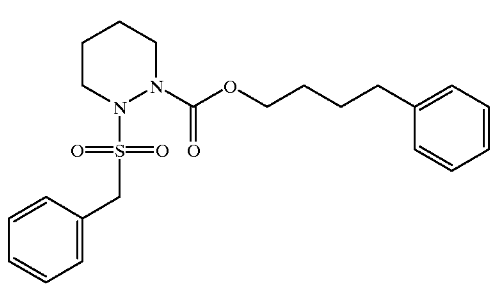 | 4-phenylbutyl 2-[benzylsulfonyl]-perhydropyridazine-carboxylate |

-continued
| No. | Structure | Name |
|---|---|---|
| 20 | 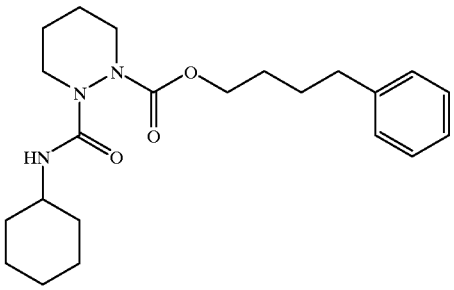 | 4-phenylbutyl 2-(N-cyclohexylcarbamoyl)-perhydropyridazine-carboxylate |
| 21 | 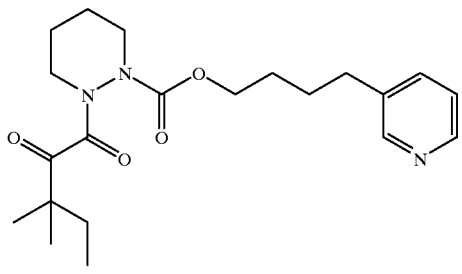 | 4-(3-pyridyl)butyl 2-(3,3-dimethy-2-oxopentanoyl)-perhydropyridazine-carboxylate |
| 22 | 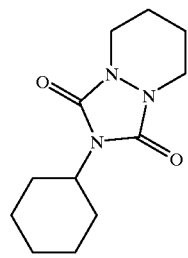 | 2-cyclohexyl-2,5,6,7,8,8a-hexahydro-2,8a-diazaindolizine-1,3-dione |
| 23 | 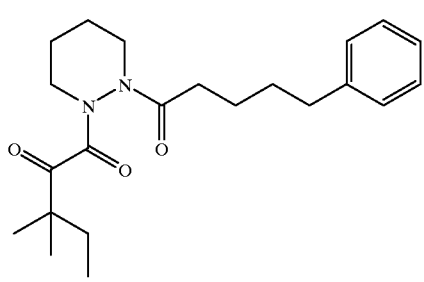 | 3,3-dimethyl-1-[2-({5-phenyl}pentanoyl)-perhydropyridazinyl]-pentane-1,2-dione |
| 24 | 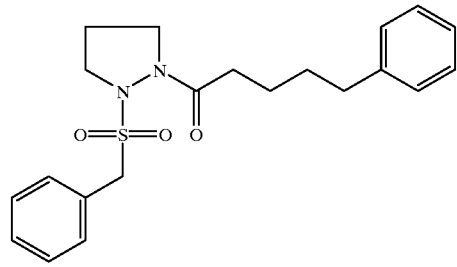 | 1-(5-phenylpentanoyl)-2-(benzylsulfonyl)-tetrahydro-1H-1-pyrazole |

| No. | Structure | Name |
|---|---|---|
| 25 | 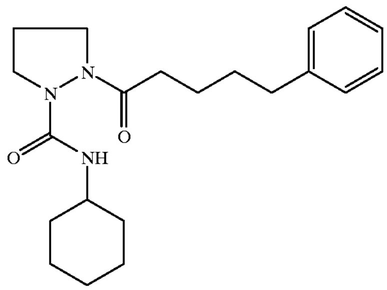 | 1-(5-phenylpentanoyl)-2-(N-cyclohexyl-carbamoyl)tetrahydro-1H-1-pyrazole |
| 26 | 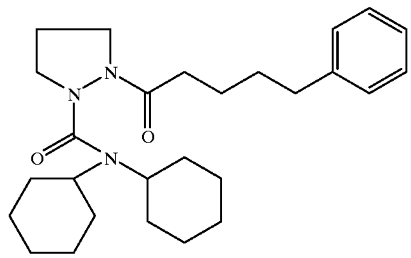 | 1-(5-phenylpentanoyl)-2-(N,N-dicyclohexyl-carbamoyl)tetrahydro-1H-1-pyrazole |

The compounds of this invention possess at least one asymmetric center and thus can be produced as mixtures of stereoisomers or as individual R- and S-stereoisomers. The individual enantiomers may be obtained by using an optically active starting material, by resolving a racemic or non-racemic mixture of an intermediate at some appropriate stage of the synthesis, or by resolving a compound of the present invention. It is understood that the individual R- and S- stereoisomers as well as mixtures (racemic and non-racemic) of stereoisomers are encompassed by this invention.

PHARMACEUTICAL COMPOSITIONS OF THE PRESENT INVENTION

The present invention also relates to a pharmaceutical composition comprising:
(i) an effective amount of a compound of the present invention, as defined above; and
(ii) apharmaceutically acceptable carrier.
Preferably, the compound is present in an effective amount for effecting a neuronal activity.

METHODS OF THE PRESENT INVENTION

METHODS FOR EFFECTING NEURONAL ACTIVITIES

The present invention further relates to a method for effecting a neuronal activity in a mammal, comprising administering to said mammal an effective amount of a compound of the present invention, as defined above.

The neuronal activity that is effected by the inventive method may be selected from the group consisting of stimulation of damaged neurons, promotion of neuronal regeneration, prevention of neurodegeneration and treatment of a neurological disorder.

Examples of neurological disorders that are treatable by the methods of the present invention include without limitation: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barre syndrome; Alzheimer's disease; Huntington's disease; and Parkinson's disease.

The inventive method is particularly useful for treating a neurological disorder selected from the group consisting of peripheral neuropathy caused by physical injury or disease state, traumatic brain injury, physical damage to spinal cord, stroke associated with brain damage, demyelinating disease and neurological disorder relating to neurodegeneration.

Examples of neurological disorders relating to neurodegeneration include Alzheimer's disease, Parkinson's disease, Huntinaton's disease and amyotrophic lateral sclerosis (ALS).

METHODS FOR TREATING ALOPECIA OR PROMOTING HAIR GROWTH

The present invention further relates to a method for treating alopecia in a mammal, comprising administering to the mammal an effective amount of a compound of the present invention, as defined above.

METHODS FOR TREATING VISION DISORDERS OR IMPROVING VISION

The present invention further relates to a method for treating a vision disorder, promoting vision regeneration or improving vision in a mammal, comprising administering to the mammal an effective amount of a compound of the present invention, as defined above.

Preferably, the vision disorder is a disorder of optic nerve or visual pathway.

METHODS FOR TREATING MEMORY IMPAIRMENT OR ENHANCING MEMORY PERFORMANCE

The present further relates to a method for treating memory impairment or enhancing memory performance in a mammal, comprising administering to the mammal an effective amount of a compound of the present invention, as defined above.

METHODS FOR PREPARING INVENTIVE COMPOUNDS

The compounds of the present invention can be readily prepared by standard techniques of organic chemistry, utilizing the general synthetic pathways depicted below in Schemes I and II.

SCHEME 1

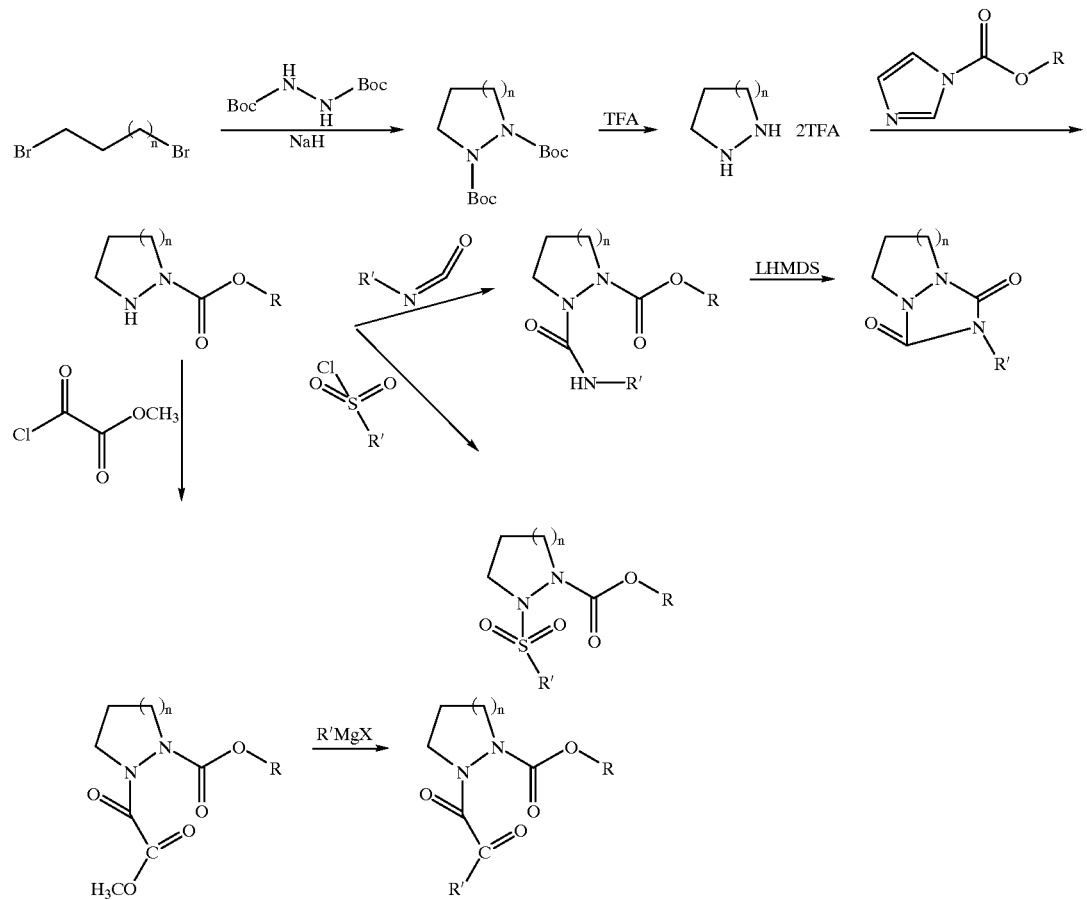

SCHEME 2

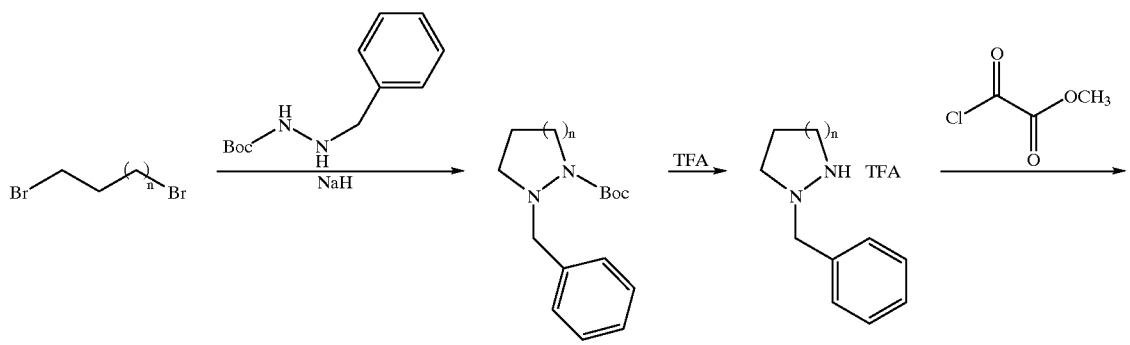

-continued

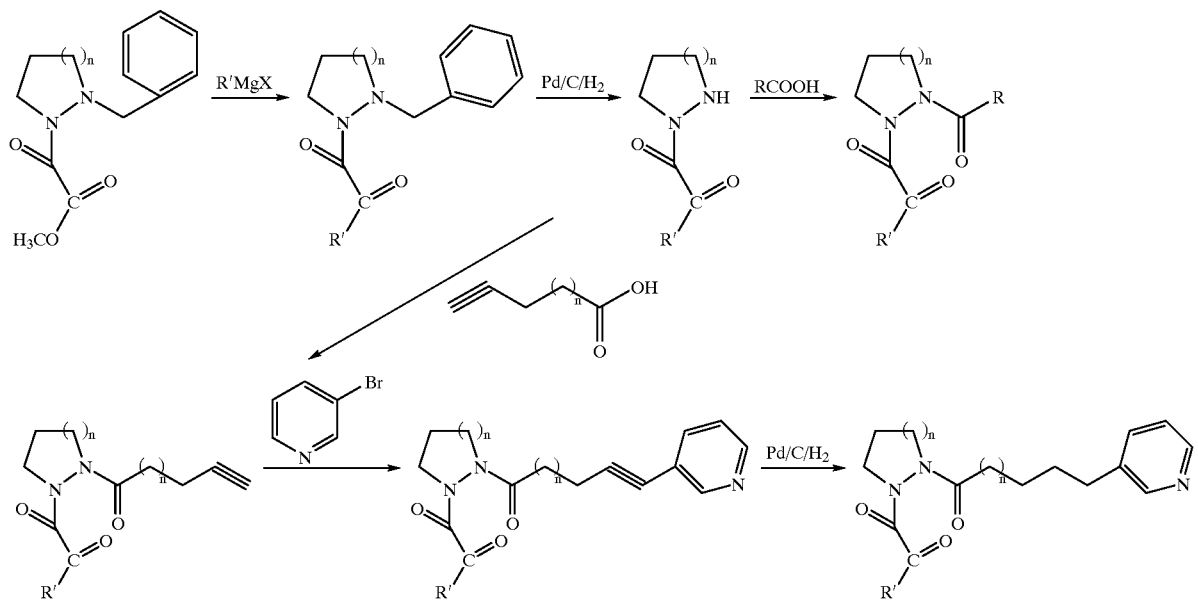

ROUTE OF ADMINISTRATION

The substituent R depicted in Schemes 1 and 2 above has the definition: —$CR_3$, —$COOR_3$, —$COR_3$, —$COSR_3$, —$CSSR_3$, —$CSOR_3$, —$SO_3H$, —$SO_2HNR_3$, —CN, —$PO_2(R_3)_2$, —$PO_3(R_3)_2$, —$OR_3$, —$SR_3$, —$NHCOR_3$, —$N(R_3)_2$, —$CON(R_3)_2$, —$CSN(R_3)_2$, —$CON(H)$—$OR_3$, —$CONHNHSO_2R_3$, —$COHNSO_2R_3$, —$CONR_3CN$,

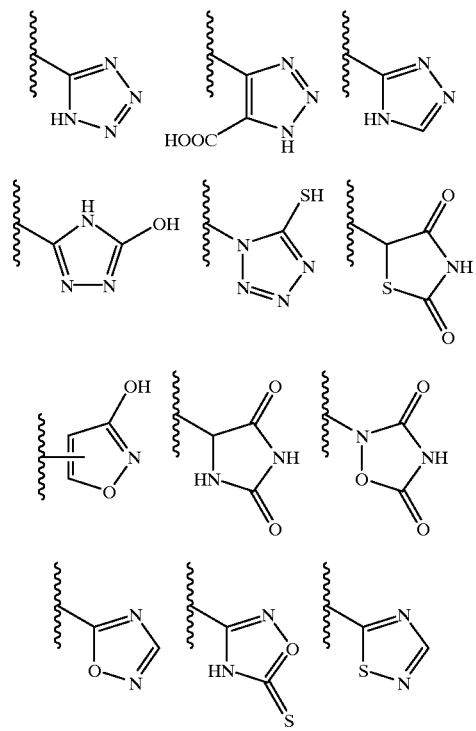

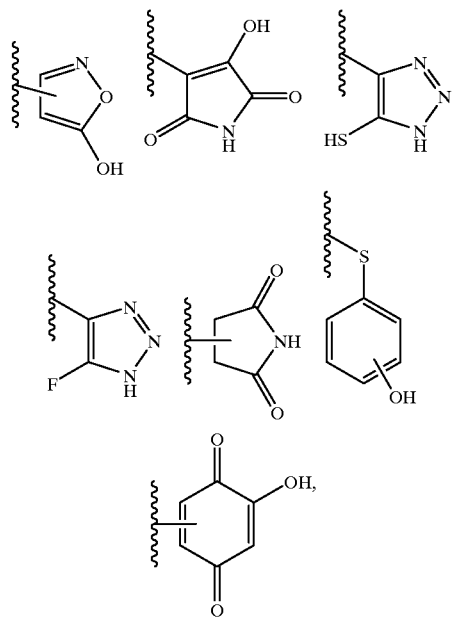

wherein said R group is unsubstituted or substituted with one or more substituents); and $R_3$ is independently hydrogen, $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s).

Additionally, the substituent R' in Schemes 1 and 2 above has the definition:

hydrogen, $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s).

In the inventive methods, the compounds will generally be administered to a patient in the form of a pharmaceutical formulation. Such formulation preferably includes, in addition to the active agent, a physiologically acceptable carrier and/or diluent. The compounds may be administered by any means known to an ordinarily skilled artisan. For example, the compounds may be administered orally, parenterally, by inhalation spray, topically, rectally, nasally, buccally, vaginally, directly into the middle or inner ear, or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal, intracranial, intracerebral, intraosseous, infusion, transdermal, transpulmonary routes.

To be effective therapeutically as central nervous system targets, the compounds should readily penetrate the blood-brain barrier when peripherally administered. Compounds which cannot penetrate the blood-brain barrier can be effectively administered by an intraventricular route.

DOSAGE

The compounds and compositions of the present invention may be administered by a single dose, multiple discrete doses or continuous infusion. The compounds are well suited to continuous infusion. Pump means, particularly subcutaneous pump means, are preferred for continuous infusion.

Dose levels on the order of about 0.1 mg to about 10,000 mg of the active ingredient compound, but less than 40 mg/kg where the compound is Suramin, are useful in the treatment of the above conditions, with preferred levels being about 0.1 mg to about 1,000 mg. The specific dose level for any particular patient will vary depending upon a variety of factors, including the activity and the possible toxicity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

ADMINISTRATION REGIMEN

For the methods of the present invention, any administration regimen well known to an ordinarily skilled artisan for regulating the timing and sequence of drug delivery can be used and repeated as necessary to effect treatment. Such regimen may include pretreatment and/or co-administration with additional therapeutic agents.

CO-ADMINISTRATION WITH OTHER TREATMENTS

The compounds and compositions of the present invention may be used alone or in combination with one or more additional agent(s) for simultaneous, separate or sequential use.

The additional agent(s) may be any therapeutic agent(s) known to an ordinarily skilled artisan, including without limitation: one or more compound(s) of the present invention; and one or more neurotrophic factor(s) selected from the group consisting of neurotrophic growth factor, brain derived growth factor, glial derived growth factor, cilial neutrophic factor, insulin growth factor, acidic fibroblast growth factor, basic fibroblast growth factor, platelet-derived growth factor, neurotropin-3, neurotropin-4 and neurotropin-5; one or more neopsic factors.

The compounds of the present invention can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a compound of the present invention, as well as one or more pharmaceutical excipients, such as wetting, emulsifying and pH buffering agents.

EXAMPLES

The following examples are illustrative of the present invention and are not intended to be limitations thereon.

Example 1

Synthesis of 4-Phenylbutyl 2-(3,3-dimethyl-2-oxopentanoyl)perhydropyridazinecarboxylate (Compound 17)

a. Synthesis of tert-butyl 2-[(tert-butyl)oxycarbonyl]-perhydropyridazinecarboxylate A solution of di-Boc hydrazine (20 g, 84.4 mmol) in 150 DMF was added dropwise to a suspended solution of 6.75g (168.8 mmol) NaH in 75 ml DMF under nitrogen. After the mixture was stirred for 30 minutes at room temperature, a solution of 1,4 dibromobutane (18.2 g, 84.4 mmol) in 25 ml DMF was added dropwise. The reaction was allowed to stir overnight at room temperature. The reaction was then concentrated, followed by partition between 200 ml $CH_2Cl_2$ and 200 ml water. The aqueous layer was extracted with additional 200 ml $CH_2Cl_2$. The combined organic layers were dried over MgSO4, and filtered and concentrated. The crude product was further purified by silica gel chromatography to yield 20.2 g (82% yield) product. The product was analyzed by GC/MS as pure compound with $M^+$ 286.

b. Synthesis of perhydropyridazine 2.83 ml (36.7 mmol) TFA was added dropwise to a solution of tert-butyl 2-[(tert-butyl)oxyarbonyl] perhydropyridazinecarboxylate (1.5 g, 5.2 mmol) in 7 ml $CH_2Cl_2$, and the mixture was stirred overnight. At this time, the reaction was completed and 5.85 ml (42 mmol) triethylamine was added to quench the reaction. The reaction was concentrated and the residue, which contained product, was used without further purification.

c. Synthesis of 4-phenylbutyl perhydropyridazine-carboxylate

A solution containing 1,1' carbonyl diimidazole (0.893 g, 5.5 mmol) in 5 ml $CH_2Cl_2$ was added slowly to a solution of $CH_2Cl_2$ containing phenylbutyl alcohol (0.89 ml, 5.77 mmol). After stirring at room temperature for 1 hour, this solution was then added slowly to a solution containing perhydropyridazine mentioned above. The reaction was allowed to stir for overnight. The crude mixture was then concentrated and used without further purification.

d. Synthesis of methyl 2-oxo-2-{2-[(4-phenylbutyl)oxy-carbonyl]perhydropyridazinyl} acetate A solution of $CH_2Cl_2$ containing previous crude product of 4-phenylbutyl perhydropyridazinecarboxylate from last step was cooled to 0° C., and a solution of methyl oxalyl chloride (0.74 g, 5.77 mmol) in 5 ml CH$_2$Cl$_2$ was added dropwise over 0.5 hour. The resulting mixture was stirred at 0° C. for 4 hours, and then warmed up to room temperature. The reaction mixture was diluted with 50 ml CH$_2$Cl$_2$ and washed with water. The organic layer was dried over MgSO$_4$, and filtered and concentrated. The. crude product was further purified by silica chromatography to yield 1.8 g (62% overall yield for three steps) product. $^1$H NMR (CDCl$_3$, 400 MHz): δ 1.39 (m, 2H); 1.69 (m, 6H); 2.62 (t, 2H, J=8); 2.83 (m, 1H); 3.10 (m, 1H); 3.79 (s, 3H); 4.16 (m, 3H); 4.31 (m, 1H); 7.22 (m, 5H).

e. Synthesis of 4-phenylbutyl 2-(3,3-dimethyl-2-oxopentanoyl)perhydropyridazine carboxylate A solution of methyl 2-oxo-2-{2-[(4-phenylbutyl)-oxycarbonyl]perhydropyridazinyl} acetate (1.2 g, 3.45 mmol) in 15 ml dry THF was cooled to −78° C. and treated with 5.2 ml of 1.0 M solution of 1,1-dimethylpropylmagnesium chloride in THF. After stirring the resulting homogeneous mixture at −780° C. for 4 hours, the mixture was poured into saturated ammonium chloride (20 ml) and extracted into ethyl acetate. The organic layer was washed with water, dried and concentrated. The crude material was purified by silica gel column, eluting with 25% ethyl acetate in hexane, to obtain 0.98 g product (73% yield). R$_f$=0.73 (2:1 hexane:EtOAc). $^1$H NMR (CDCl$_3$, 400 MHz): δ 0.81 (t, 3H, J=7.1); 1.13 (s, 3H); 1.20 (s, 3H); 1.64 (m, 10H); 2.64 (m, 2H); 2.86 (m, 1H); 3.20 (m, 1H); 3.99 (m, 1H); 4.19 (m, 2H); 4.35 (m, 1H); 7.24 (m, 5H). Anal. Calcd. for C$_{22}$H$_{32}$N$_2$O$_4$: C, 68.01; H, 8.30; N, 7.21. Found: C, 68.10; H, 8.29; N, 7.15.

Example 2

Synthesis of 4-Phenylbutyl 2-[benzylsulfonyl]-perhydropyridazinecarboxylate (Compound 19)

A solution of α-toluene sulfonyl chloride (1.12 g, 5.77 mmol) in CH$_2$Cl$_2$ was added to a CH$_2$Cl$_2$ solution containing 4-phenylbutyl perhydropyridazinecarboxylate (1.37 g, 5.2 mmol) and triethylamine (0.83 ml, 6 mmol). The reaction was stirred overnight at room temperature under nitrogen atmosphere, and then diluted to 50 ml CH$_2$Cl$_2$. The organic layer was washed with water, dried, and concentrated. The crude material was purified by silica gel column to yield 1.4 g (64w) final product as clear oil. R$_f$=0.60 (2:1 hexane:EtOAc). $^1$H NMR (CDCl$_3$, 400 MHz): δ 1.68 (m, 8H) 2.67 (m, 2H); 2.90 (m, 1H); 3.38 (m, 2H); 4.22 (m, 5H) 7.32 (m, 10H). Anal. Calcd. for C$_{22}$H$_{28}$N$_2$S$_1$O$_4$: C, 63.44; H, 6.78; N, 6.73, S, 7.70. Found: C, 63.86; H, 6.83; N, 6.41, S, 7.58.

Examle 3

Synthesis of 4-Phenylbutyl 2-(N-cyclohexylcarbamoyl)-perhydroyridazinecarboxylate (Compound 20)

Cyclohexylisocyanate (0.38 g, 3.0 mmol) was added to a CH$_2$Cl$_2$ solution containing 4-phenylbutyl perhydropyridazinecarboxylate (0.72 g, 2.75 mmol) and triethylamine (0.42 ml, 3 mmol). The reaction was stirred overnight at room temperature under nitrogen atmosphere, and then diluted to 50 ml CH$_2$Cl$_2$. The organic layer was washed with water, dried, and concentrated. The crude material was purified by silica gel column to yield 0.95 g (89%) final product as clear oil. R$_f$=0.28 (2:1 hexane:EtOAc). $^1$H NMR (CDCl$_3$, 400 MHz): δ 1.10 (m, 3H); 1.33 (m, 3H); 1.69 (m, 10H); 1.88 (m, 2H); 2.62 (m, 2H); 2.72 (m, 1H); 2.87 (m, 1H); 3.60 (m, 1H); 4.13 (m, 3H); 4.38 (m, 1H); 5.11 (d, 1H, J=8.3); 7.23 (m, 5H). Anal. Calcd. for C$_{22}$H$_{28}$N$_3$O$_3$-0.14H$_2$O: C, 67.75; H, 8.60; N, 10.77. Found: C, 67.75; H, 8.45; N, 10.90.

Example 4

Synthesis of 3,3-Dimethyl-1-[2-(6-phenylhexanoyl)perhydropyridazinyl]pentane-1,2-dione (Compound 14) Using Scheme 2 a. Synthesis of (tert-butoxy)-N-[benzylamino]formamide

A solution of benzyl carbazate (25 g, 150.4 mmol), Boc anhydride (42.7 g, 195.5 mmol), triethylamine (19.8 g, 195.5 mmol), DMAP (0.9 g, 7.5 mmol) in 650 ml CH$_2$Cl$_2$ was stirred for 24 hours. The mixture was concentrated and purified by silica gel column, eluting with 20% ethyl acetate in hexane, to yield 36 g (90%) product. $^1$H NMR (CDCl$_3$, 400 MHz): δ 1.40 (m, 9H); 5.25 (m, 2H); 7.36 (m, 5H).

b. Synthesis of tert-butyl 2-benzylperhydropyridazine-carboxylate

A solution of (tert-butoxy)-N-[benzylamino]formamide (35 g, 131 mmol) in 300 DMF was added dropwise to a suspended solution of 6.3 g (262 mmol.) NaH in 130 ml DMF under nitrogen. After the mixture was stirred for 30 minutes at room temperature, a solution of 1,4 dibromobutane (28.4 g, 131 mmol) in 50 ml DMF was added dropwise. The reaction was allowed to stir overnight at room temperature. The reaction was then concentrated, followed by partition between 200 ml CH$_2$Cl$_2$ and 200 ml water. The aqueous layer was extracted with additional 200 ml CH$_2$Cl$_2$. The combined organic layers were dried over MgSO$_4$, and filtered and concentrated. The crude product was further purified by silica chromatography to yield 13.5 g (32% yield) product. $^1$H NMR (CDCl$_3$, 400 MHz) δ 1.46 (m, 9H); 1.64 (m, 4H); 2.88 (m, 2H); 4.20 (m, 2H); 5.16 (m, 2H); 7.31 (m, 5H).

c. Synthesis of methyl 2-oxo-2-[2-benzylperhydropyridazinyl]acetate 20% TFA in CH$_2$Cl$_2$ was cooled to 0° C. and added dropwise to a solution of tert-butyl 2-benzylperhydropyridazinecarboxylate (13.34 g, 41.7 mmol) in 10 ml CH$_2$Cl$_2$. The mixture was stirred overnight. At this time, the mixture was cooled to 0° C. and 12.66 ml (125 mmol) triethylamine was added, followed by addition dropwise of methyl oxalyl chloride (5.62, 45.9 mmol) in 5 ml CH$_2$Cl$_2$. The mixture was allowed to stirred 2 hours at 0° C. and warmed up to room temperature overnight. The reaction was diluted with addition of CH$_2$Cl$_2$ and washed with water. The organic layer was dried over MgSO$_4$, and filtered and concentrated. The crude product was further purified by silica chromatography to yield 9.2 g (72.4% yield) product as clear oil. $^1$H NMR (CDCl$_3$, 400 MHz): δ 1.72 (m, 4H); 2.85 (m, 1H); 3.12 (m, 1H); 3.67 (s, 3H); 4.15 (m, 1H); 4.35 (m, 1H); 5.20 (m, 2H); 7.35 (m, 5H)

d. Synthesis of 3,3-dimethyl-1-[2-benzylperhydropyridazinyl]pentane-1,2-dione

A solution of methyl 2-oxo-2-[2-benzylperhydropyridazinyl]acetate (9.0 g, 29.4 mmol) in 30 ml dry THF was cooled to −78° C. and treated with 35 ml of 1.0 M solution of 1,1-dimethylpropylmagnesium chloride in THF. After stirring the resulting homogeneous mixture at for 5 hours, the mixture was poured into saturated. ammonium chloride (150 ml) and extracted into ethyl acetate. The organic layer was washed with water, dried and concentrated. The crude material was purified by silica gel column, eluting with 10% ethyl acetate in hexane, to obtain 7.0 g product (69% yield) as clear oil. $^1$H NMR (CDCl$_3$, 400 MHz): δ 0.76 (t, 3H, J=7.0); 1.06 (s, 6H); 1.69 (m, 6H); 2.80 (m, 1H); 3.15 (m, 1H), 4.03 (m, 1H); 4.13 (m, 1H), 5.18 (m, 2H), 7.36 (m, 5H).

e. Synthesis of 3,3-dimethyl-1-perhydropyridazinylpentane-1,2-dione 1 g 10% Pd/C was added to a solution of 3,3-dimethyl-1-[2-benzylperhydropyridazinyl]pentane-1,2-dione (7.0 g, 20.2 mmol) in 70 ml EtOH. The mixture was under hydrogenation at room pressure (1 atm) overnight. The product was obtained as white solid after filtering Pd catalyst and concentration (3.8 g, 89%). $^1$H NMR (CDCl$_3$, 400 MHz) δ 0.88 (t, 3H, J=7.0); 1.19 (s, 6H); 1.65 (m, 4H); 1.79 (m, 2H); 2.85 (m, 2H); 3.42 (m, 1H); 3.56 (m, 1H).

f. Synthesis of 3,3-dimethyl-1-[2-(6-phenylhexanoyl)-perhydropyridazinyl]pentane-1,2-dione To a solution of 5-phenylvalaric acid (0.2 g, 1.1 mmol) in 3 ml CH$_2$Cl$_2$ was added triethylamine (0.15 ml, 1.1 mmol), followed by isobutyl chloroformate (0.15 g, 1.1 mmol) at 0° C. After stirring for 5 minutes, a solution of 3,3-dimethyl-1-perhydropyridazinylpentane-1,2-dione (0.212 g, 1 mmol) in 1 ml CH$_2$Cl$_2$ was added. The reaction was gradually warmed up to room temperature. The crude material was subject to silica gel purification to yield final product as clear oil (0.20 g, 55%). R$_f$=0.58 (33% EtOAc/hexane). $^1$H NMR (CDCl$_3$, 400 MHz): δ 0.89 (t, 3H, J=7.5); 1.24 (s, 6H); 1.37 (m, 2H); 1.68 (m, 6H); 1.74 (m, 4H); 2.23 (m, 2H); 2.62 (t, 2H, J=7.60); 2.80 (m, 2H); 4.53 (m, 2H); 7.21 (m, 5H). Anal. Calcd. for C$_{23}$H$_{24}$N$_2$O$_3$: C, 71.47; H, 8.87; N, 7.25. Found: C, 71.54; H, 8.80; N, 7.32.

Example 5

Synthesis of 3,3-Dimethyl-1-2-[6-(3-pyridyl) hexanoyl)-perhydropyridazinyl]-pentane-1,2-dione (Compound 15) Using Scheme 2 a. Synthesis of 1-(2-hex-5-ynoylperhydropyridazinyl)-3,3-dimethylpentane-1,2-dione To a solution of 5-hexynoic acid (0.467 g, 4 mmol) in 10 ml CH$_2$Cl$_2$ was added triethylamine (0.56 ml, 4 mmol), followed by isobutyl chloroformate (0.53 ml, 4 mmol) at 0° C. After stirring for 5 minutes, a solution of 3,3-dimethyl-1-perhydropyridazinyl pentane-1,2-dione (0.424 g, 2 mmol) in 1 ml CH$_2$Cl$_2$ was added. The reaction was gradually warmed up to room temperature. The crude material was subject to silica gel purification to yield final product as clear oil (0.385 g, 63%). $^1$H NMR (CDCl$_3$, 400 MHz) δ 0.91 (t, 3H, J=7.0); 1.26 (s, 6H); 1.76(m, 8H); 2.28 (m, 2H); 2.50 (m, 2H); 2.88 (m, 2H); 3.60 (m, 1H); 4.50 (m, 2H).

b. Synthesis of 3,3-dimethyl-1-[2-(6-(3-pyridyl)hex-5-ynoyl)perhydropyridazinyl]pentane-1,2-dione To a solution of 1-(2-hex-5-ynoylperhydropyridazinyl)-3,3-dimethylpentane-1,2-dione (0.384 g, 1.25 mmol) in 10 ml CH$_2$Cl$_2$ under nitrogen was added 3-iodopyridine (0.283 g, 1.38 mmol), (Ph$_3$P)$_2$PdCl$_2$ (0.044 g, 0.06 mmol), CuI (0.0024 g, 0.013 mmol) and triethylamine (0.3 ml, 2 mmol). The reaction mixture was stirred 30 minutes at room temperature and then refluxed overnight. The mixture was concentrated and purified by silica gel column, eluting with 30% ethyl acetate in hexane, to yield product as light yellow oil (0.31 g, 65%). $^1$H NMR (CDCl$_3$, 400 MHz) δ 0.84 (t, 3H, J=7.4); 1.21 (s, 6H); 1.70 (m, 6H); 1.96(m, 2H), 2.52 (m, 3H); 2.90 (m, 2H); 3.60 (m, 1H); 4.42 (m, 2H); 7.20 (m, 1H); 7.66 (m, H); 8.49 (m, 1H); 8.62 (m, 1H).

c. Synthesis of 3,3-dimethyl-1-[2-(6-(3-pyridyl)-hexanoyl) perhydropyridazinyl]pentane-1,2-dione 0.1 g PtO$_2$ was added to a solution of 3,3-dimethyl-1-[2-(6-(3-pyridyl)hex-5 ynoyl)perhydropyridazinyl]pentane-1, 2-dione (0.3 g, 0.8 mmol) in 20 ml dry MeOH. The mixture was under hydrogenation at room pressure (1 atm) overnight. The product was obtained as clear oil after filtering the catalyst, concentration and purifying on a silica gel (0.125 g, 41%). R$_f$=0.18 (EtOAc). $^1$H NMR (CDCl$_3$, 400 MHz): δ 0.89 (t, 3H, J=7.4); 1.24 (s, 6H); 1.38 (m, 2H); 1.66 (m, 10H); 2.14 (m, 2H); 2.63 (m, 2H); 2.82 (m, 2H); 4.60 (m, 2H); 7.23 (m, 4H). Anal. Calcd. for C$_{22}$H$_{33}$N$_3$O$_3$: C, 68.19; H, 8.58; N, 10.84. Found: C, 68.40; H, 8.52; N, 10.62.

Example 6

Synthesis of 2-Cyclohexyl-2,5,6,7,8,8a-hexahydro-2,8adiazaindolizine-1,3-dione (Compound 22) using Scheme 1

To a solution of 4-phenylbutyl 2-(N-cyclohexyl-carbamoyl)perhydropyridazine carboxylate (0.53 g, 1.37 mmol) in 5 ml THF at 0° C. under nitrogen was added 1.37 ml of 1 M LHMDS in THF. The mixture was allowed to stir overnight, gradually warming up to room temperature. The mixture was concentrated and purified by silica gel column, eluting with 30% ethyl acetate in hexane, to afford product (0.27 g, 83%). R$_f$=0.32 (2:1 hexane:EtOAc). $^1$H NMR (CDCl$_3$, 400 MHz): δ 1.27(m 3H); 1.75(m, 9H); 2.12(m, 2H); 3.50(m, 4H); 3.87(m, 1H). Anal. Calcd. for C$_{12}$H$_{19}$N$_3$O$_2$: C, 60.74; H, 8.07; N, 17.71. Found: C, 60.61; H, 8.11; N, 17.82.

Example 7

Synthesis of Compounds 1, 2, 5, 6 and 23

Compounds 1, 2, 5, 6 and 23 were synthesized by the general method illustrated in Scheme 2 and exemplified in Example 4.

1) 3,3-Dimethyl-N-[2-(5-phenylpentanoyl)tetrahydro-1H-1-pyrazolyl]-1,2-pentane-dione. R$_f$=0.25 (2:1 hexane:EtOAc). $^1$H NMR (CDCl$_3$, 300 MHz): δ 0.81–0.83 (m, 3H); 1.14 (s, 6H); 1.21 (m, 2H); 1.55–1.62 (m, 8H); 2.02 (m, 2H); 2.61 (m, 4H); 7.14–7.28 (m, 5H). Anal. Calcd. for C$_{21}$H$_{30}$N$_2$O$_3$: C, 70.36; H, 8.44; N, 7.81. Found: C, 70.10; H, 8.41; N, 7.77.

2) 3,3-Dimethyl-N-[2-(5-phenylpropanoyl)tetrahydro-1H-1-pyrazolyl]-1,2-pentanedione. R$_f$=0.60 (2:1 hexane:EtOAc). $^1$HNMR (CDCl$_3$, 300 MHz): δ 0.80–0.85 (t, 3H); 1.11–1.15 (m, 8H); 1.58–2.02 (m, 6H); 2.50–2.95 (m, 4H); 7.17–7.28 (m, 5H). Anal. Calcd. for C$_{19}$H$_{26}$N$_2$O$_3$: C, 69.06; H, 7.93; N, 8.48. Found: C, 68.98; H, 7.90; N, 8.41.

5) 3,3-Dimethyl-1-[2-(4-phenylbutanoyl)pyrazolidinyl]-pentane-1,2-dione. R$_f$=0.5 (Hexane:EtAc 1:1). $^1$H NMR (CDCl$_3$, 400 MHz): δ 0.87 (t, 3H, J=7.5); 1.22 (s, 3H); 1.26 (s, 3H); 1.64 m, 2H); 1.92–2.07 (m, H); 2.20 (m, 1H), 2.63 (m, 2H); 3.25 (m, 2H); 3.80 (m, 2H); 7.27 (m, 5H, aromatic). Anal. Calcd. for C$_{20}$H$_{28}$N$_2$O$_3$: C, 69.05 (69.02); H, 8.27 (8.22); N, 8.06 (8.05).

6) 3,3-Dimethyl-1-[2-(6-phenylhexanoyl)pyrazolidinyl]-pentane-1,2-dione. R$_f$=0.5 (Hexane:EtAc 1:1). $^1$H NMR (CDCl$_3$, 400 MHz): δ 0.87 (t, 3H, J=7.5); 1.22 (s, 3H); 1.26 (s, 3H); 1.35 (m, 2H); 1.59 (m, 6H); 2.07 (m, 2H), 2.20 (m, 1H), 2.60 (m, 3H); 3.25 (m, 2H); 3.70 (m, 2H); 7.26 (m, 5H, aromatic). Anal. Calcd. for C$_{24}$H$_{32}$N$_2$O$_3$: C, 70.65 (70.94); H, 8.70 (8.66); N, 7.36 (7.52).

3,3-Dimethyl-1-[2-({5-phenyl}pentanoyl)perhydro-pyridazinyl]pentane-1,2-dione. R$_f$=0.53 (33% EtOAc/hexane). $^1$H NMR (CDCl$_3$, 400 MHz): δ 0.90 (t, 3H, J=7.44); 1.24 (s, 6H); 1.64 (m, 8H); 2.28 (m, 2H); 2.65 (m, 2H); 2.80 (m, 2H); 3.12 (m, 1H); 3.58 (m, 1H); 4.54 (m,2H);

7.22 (m, 5H). Anal. Calcd. for $C_{22}H_{32}N_2O_3$: C, 70.94; H, 8.66; N, 7.52. Found: C, 71.07; H, 8.59; N, 7.51.

Example 8

Synthesis of Compounds 3, 4 and 7

Compounds 3, 4 and 7 were synthesized by the general method illustrated in Scheme 2 and exemplified by Example 5.

3) 3,3-Dimethyl-1-[2-(5-(3-pyridyl)pent-4-ynoyl)-pyrazolidinyl]pentane-1,2-dione $R_f$=0.2 (EtCAc). $^1$H NMR (CDCl$_3$, 400 MHz): δ 0.87 (t, 3H, J=7.5); 1.22 (s, 3H); 1.26 (s, 3H); 1.63 (m, 2H); 2.1 (m, 2H); 2.73 (m, 4H); 3.20–3.85 (m, 4H); 7.19 (m, 1H); 7.66 (m, 1H); 8.5 (m, 2H). Anal. Calcd. for $C_{20}H_{25}N_3O_3$: C, 67.67 (64.58), H: 6.91 (7.09), N: 10.63 (10.82).

4) 3,3-Dimethyl-1-(2-pent-4-ynoylpyrazolidinyl)pentane-1,2-dione. $R_f$=0.45 (EtAc). $^1$H NMR (CDC$_3$, 400 MHz): δ 0.87 (t, J=7.5); 0.90 (m, 2H); 1.22 (s, 3H); 1.26 (s, 3H); 1.64 (m, 2H); 2.03–2.20 (m, 3H), 2.52 (m, 2H), 2.63 (m, 1H); 3.69 (m, 3H). Anal. Calcd. for $C_{15}H_{22}N_2N_2O_3$: C, 64.55 (64.73); H, 7.98 (7.97); N, 9.98 (10.06).

7) 3,3-Dimethyl-1-[2-(5-(3-pyridyl)pentanoyl)-pyrazolidinyl]pentane-1,2-dione. $R_f$=0.3 (EtAc). $^1$H NMR (CDCl$_3$, 400 MHz): δ 0.87 (t, 3H, J=7.5); 1.22 (s, 3H); 1.26 (s, 3H); 1.37 (m, 2H); 1.65 (m, 6H); 2.1 (m, 2H); 2.30 (m, 1H); 2.62 (m, 3H); 3.20–3.85 (m, 4H); 7.19 (m, 1H); 7.66 (m, 1H); 8.5 (m, 2H). Anal. Calcd. for $C_{20}H_{29}N_3O_3$: C, 65.74 (65.98); H, 8.06 (8.20); N, 11.09 (10.89).

Example 9

Synthesis of Compounds 8–10, 13, 16, 18 and 21

Compounds 8–10, 13, 16, 18 and 21 were synthesized by the general method illustrated in Scheme 1 and exemplified in Example 1.

8) 3-Phenylpropyl 2-(3,3-dimethyl-2-oxopentanayl)-pyrazolidinecarboxylate. $R_f$=0.4 (25% EtOAc/Hexane). $^1$H NMR (CDCl$_3$, 400 MHz): δ 0.86 (t, 3H, J=7.4); 1.22 (s, 6H); 1.66 (t, 2H, J=7.5); 2.00–2.12 (m, 4H); 2.72 (t, 2H, J=7.4); 3.60 (br s, 4H); 4.18 (t, 2H, J=6.5); 7.18–7.31 (m, 5H). Anal. Calcd. for $C_{20}H_{28}N_2O_4$: C, 66.64; H, 7.83; N, 7.77. Found: C, 66.73; H. 7.81; N, 7.72.

9) 3-(3-Pyridyl)propyl 2-(3,3-dimethyl-2-oxopentanoyl)-pyrazolidinecarboxylate. $R_f$=0.1 (100% EtOAc). $^1$H NMR (CDCl$_3$, 400 MHz): δ 0.85 (t, 3H, J=7.5); 1.21 (s, 6H) 1.67 (t, 2H, J=7.5); 2.00–2.13 (m, 4H); 2.72 (t, 2H, J=7.5); 3.62 (br s, 4H); 4.19 (t, 2H, J=6.4); 7.28 (br s, 1H), 7.54 (d, 1H, J=7.7); 8.48 (s, 2H). Anal. Calcd. for $C_{19}H_{27}N_3O_4$-0.35 H$_2$O: C, 62.06; H, 7.59; N, 11.43. Found: C, 61.77; H, 7.53; N, 11.36.

10) 4-Phenylbutyl 2-(3,3-dimethyl-2-oxopentanoyl)-pyrazolidinecarboxylate. $R_f$=0.6 (25% EtOAc/Hexane). $^1$H NMR (CDCl$_3$, 400 MHz): δ 0.83 (t, 3H, J=7.5); 1.19 (s, 6H); 1.67 (t, 2H, J=7.5); 1.60–1.69 (m, 4H); 2.07 (t, 2H, J=7.4); 2.62 (t, 2H, J=6.4); 3.60 (br s, 4H); 4.13 (t, 2H, J=6.1); 7.28–7.15 (m, 5H). Anal. Calcd. for $C_{21}H_{30}N_2O_4$: C, 67.35; H, 8.07; N, 7.48. Found: C, 67.54; H, 8.31; N, 7.40.

13) 2-Phenylethyl 2-(3,3-dimethyl-2-oxopentanoyl)-pyrazolidinecarboxylate. $R_f$=0.5 (25% EtOAc/Hexane). $^1$H NMR (CDCl$_3$, 400 MHz): δ 0.83 (tr 3H, J=7.5); 1.18 (s, 6H); 1.63 (m, 2H); 1.99 (m, 2H); 2.97 (t, 2H, J=7.1); 3.60 (br s, 4H); 4.35 (t, 2H, J=6.6); 7.19–7.30 (m, 5H). Anal. Calcd. for $C_{17}H_{26}N_2O_4$: C, 65.88; H, 7.56; N, 8.09. Found: C, 65.82; H, 7.51; N, 8.02.

16) 3-phenylpropyl 2-(3,3-dimethyl-2-oxopentanoyl)-perhydropyridazinecarboxylate. $R_f$=0.73 (2:1 hexane:EtOAc). $^1$H NMR (CDCl$_3$, 400 MHz): 0.82 (t, 3H, J=7.4); 1.16 (s, 3H); 1.22 (s, 3H); 1.67 (m, 6H); 2.00 (m, 2H); 2.69 (t, 2H, J=7.9); 2.86 (m, 1H); 3.23 (m, 1H); 4.00 (m, 1H); 4.20 (m, 2H); 4.37 (m, 1H); 7.23 (m, 5H). Anal. Calcd. for $C_{21}H_{30}N_2O_4$: C, 67.35; H, 8.07; N, 7.48. Found: C, 67.51; H, 8.11; N, 7.39.

18) 5-Phenylpentyl 2-(3,3-dimethyl-2-oxopentanoyl)-perhydropyridazinecarboxylate. $R_f$=0.74 (2:1 hexane:EtOAc). $^1$H NMR (CDCl$_3$, 400 MHz): δ 0.82 (t, 3H, J=7.4); 1.14 (s, 3H); 1.21 (s, 3H); 1.38 (m, 2H); 1.65 (m, 10H); 2.62 (t, 2H, J=7.6); 2.83 (m, 1H); 3.20 (m, 1H); 3.98 (m, 1H); 4.15 (m, 2H); 4.33 (m, 1H); 7.23 (m, 5H). Anal. Calcd. for $C_{23}H_{34}N_2O_4$: C, 68.63; H, 8.51; N, 6.96. Found: C, 68.70; H, 8.47; N, 7.08.

21) 4-(3-Pyridyl)butyl 2-(3,3-dimethy-2-oxopentanoyl)-perhydropyridazinecarboxylate. $R_f$=0.45 (100% EtOAc). $^1$H NMR (CDCl$_3$, 400 MHz): δ 0.81 (t, 3H, J=7.5); 1.14 (s, 3H); 1.20 (s, 3H); 1.70 (m, 10H); 2.66 (m, 2H); 2.86 (m, 1H); 3.20 (m, 1H); 4.00 (m, 1H); 4.18 (m, 2H); 4.36 (m, 1H); 7.22 (m, 1H); 7.50 (m, 1H); 8.45 (m, 2H). Anal. Calcd. for $C_{21}H_{31}N_3O_4$-0.14 H$_2$O: C, 64.34; H, 8.04; N, 10.72. Found: C, 64.34; H, 8.02; N, 10.83.

Example 10

Synthesis of Compound 11

Compound 11 was synthesized by the general method illustrated in Scheme 1 and exemplified in Example 2.

3-Phenylpropyl 2-[benzylsulfonyl]pyrazolidine-carboxylate. $R_f$=0.5 (40% EtOAc/Hexane). $^1$H NMR (CDCl$_3$, 400 MHz): δ 2.01–2.17 (m, 4H); 2.72 (t, 2H, J=7.8); 3.68 (br s, 4H); 4.23 (t, 2H, J=6.6); 4.51 (s, 2H); 7.17–7.50 (m, 10H). Anal. Calcd. for $C_{20}H_{24}N_2SO_4$: C, 61.83; H, 6.23; N, 7.21; S, 8.25. Found: C, 61.63; H, 6.21; N, 7.05; S, 8.07.

Example 11

Synthesis of Compound 12

Compound 12 was synthesized by the general method illustrated in Scheme 1 and exemplified in Example 3.

3-Phenylpropyl 2-(N-cyclohexylcarbamoyl)pyrazolidine-carboxylate. $R_f$=0.5 (60% EtOAc/Hexane). $^1$H NMR (CDCl$_3$, 400 MHz): δ 1.09–2.00 (m, 15H); 2.69 (t, 2H, J=7.8); 3.70 (br s, 4H); 4.18 (t, 2H, J=6.4); 5.46 (d, 1H, J=8.2); 7.16–7.30 (m, 5H). Anal. Calcd. for $C_{20}H_{29}N_3O_3$: C, 66.83; H, 8.13; N, 11.69. Found: C, 66.73; H, 8.28; N, 11.59.

Example 12

$K_i$ Test

Inhibition of the peptidyl-prolyl -isomerase (rotamase) activity of the inventive compounds can be evaluated by known methods described in the literature (Harding et al., Nature, 1989, 341:758–760; Holt et al. J. Am. Chem. Soc., 115:9923–9938). These values are obtained as apparent $K_i$'s and are presented for representative compounds in Table IV. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_i$ values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

The results of these experiments are presented in TABLE I under the column "Ki".

Example 13

MPTP Model of Parkinson's Disease

The neurotrophic and neuroregenerative effects of the inventive compounds were demonstrated in an animal model of neurodegenerative disease. MPTP lesioning of dopaminergic neurons in mice was used as an animal model of Parkinson's Disease. Four week old male CD1 white mice were dosed i.p. with 30 mg/kg of MPTP for 5 days. Test compounds (4 or 10 mg/kg) or vehicle, were administered s.c. along with the MPTP for 5 days, as well as for an additional 5 days following cessation of MPTP treatment. At 18 days following MPTP treatment, the animals were sacrificed and the striata were dissected and homogenized. Immunostaining was performed on saggital and coronal brain sections using anti-tyrosine hydroxylase 1 g to quantitate survival and recovery of dopaminergic neurons. In animals treated with MPTP and vehicle, a substantial loss of functional dopaminergic terminals was observed as compared to non-lesioned animals. Lesioned animals receiving test compounds showed a significant recovery of TH-stained dopaminergic neurons.

The results of these experiments are presented in TABLE I under the column "% TH recovery".

TABLE I

| No. | Structure | Ki nM | % TH recov 4 mg/kg s.c. | % TH recov 10 mg/kg p.o. |
|---|---|---|---|---|
| 1 | 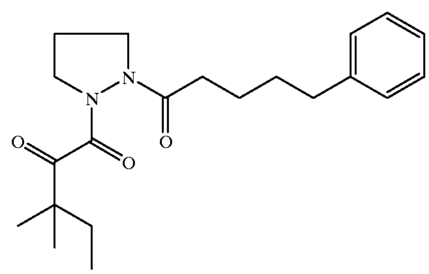 | 1175 | 14 | |
| 2 | 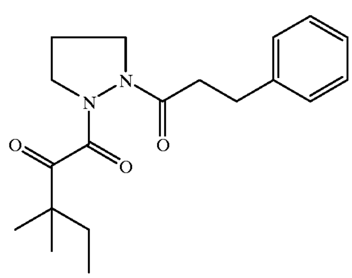 | | | 10 |
| 3 | 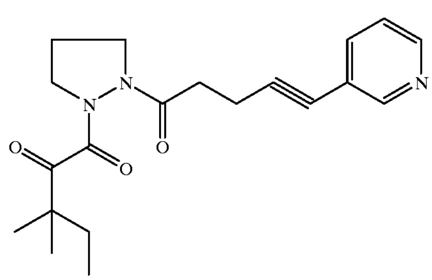 | | | 26 |

TABLE I-continued

| No. | Structure | Ki nM | % TH recov 4 mg/kg s.c. | % TH recov 10 mg/kg p.o. |
|-----|-----------|-------|--------------------------|---------------------------|
| 5   | 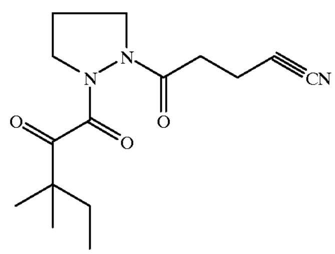          |       |                          | 4                         |
| 6   | 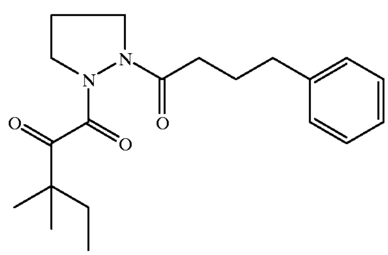          |       |                          | 32                        |
| 7   | 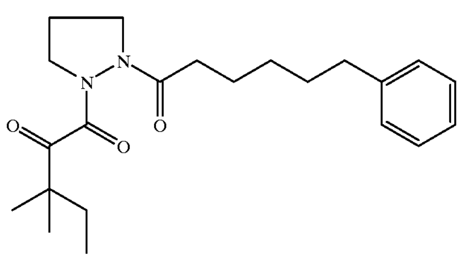          |       |                          | 57                        |
| 14  | 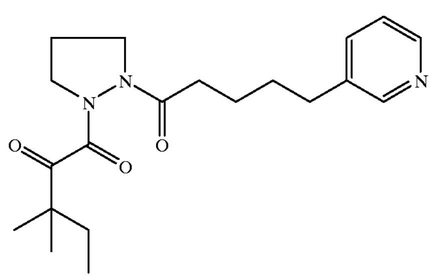          |       |                          | 35                        |
| 15  | 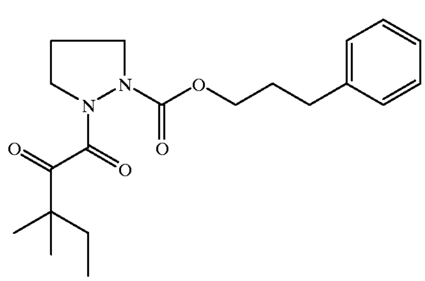          | 3208  |                          | 18                        |

TABLE I-continued

| No. | Structure | Ki nM | % TH recov 4 mg/kg s.c. | % TH recov 10 mg/kg p.o. |
|-----|-----------|-------|-------------------------|--------------------------|
| 16  | 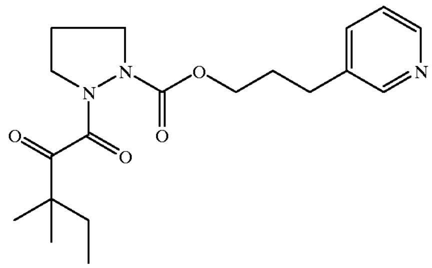          |       |                         | 3                        |
| 17  | 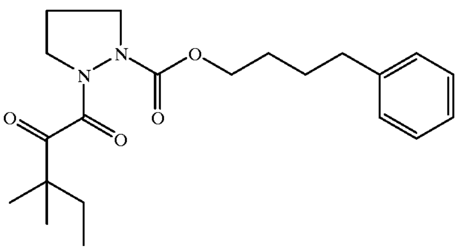          |       |                         | 21                       |
| 18  | 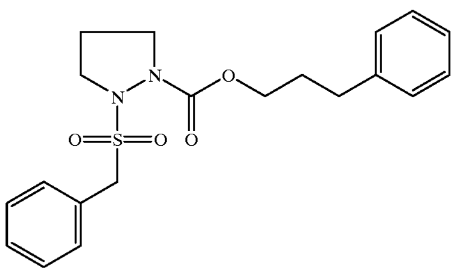          |       |                         | 49                       |
| 19  | 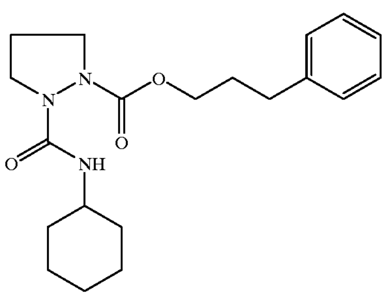          |       |                         | 23                       |
| 20  | 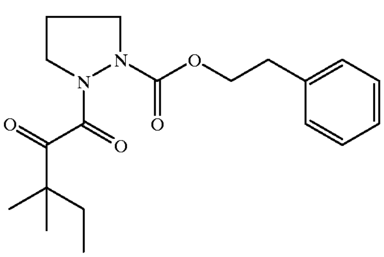          |       |                         | 46                       |

TABLE I-continued

| No. | Structure | Ki nM | % TH recov 4 mg/kg s.c. | % TH recov 10 mg/kg p.o. |
|---|---|---|---|---|
| 21 | 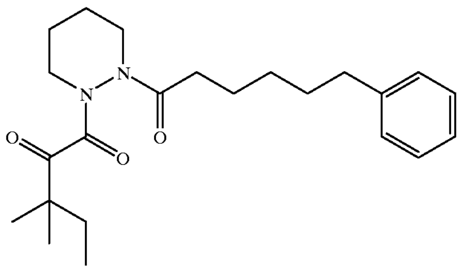 | | | 38 |
| 23 | 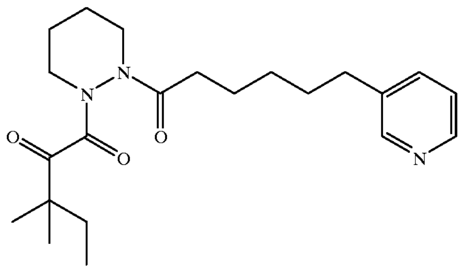 | | | 18 |

Example 13

A patient is suffering from a disease, disorder or condition described above. The patient may then be administered an effective amount of a compound of the present invention. It is expected that after such treatment, the patient would not suffer any significant injury due to, would be protected from further injury due to, or would recover from the disease, disorder or condition.

The invention being thus described, it will be obvious that the same may be varied in many ways. Such variations are not to be regarded as a departure from the spirit and scope of the invention and all such modifications are intended to be included within the scope of the following claims.

We claim:
1. A compound of formula I

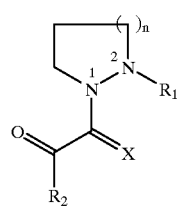

or a pharmaceutically acceptable salt, ester or solvate thereof, wherein:

n is 2;

$R_1$ is —$CR_3$, —$COOR_3$, —$COR_3$, —$COSR_3$, —$CSSR_3$, —$CSOR_3$, —$SO_3H$, —$SO_2HNR_3$, —$CN$, —$PO_2(R_3)_2$, —$PO_3(R_3)_2$, —$OR_3$, —$SR_3$, —$NHCOR_3$, —$N(R_3)_2$, —$CON(R_3)_2$, —$CSN(R_3)_2$, —$CON(H)$—$OR_3$, —$CONHNHSO_2R_3$, —$COHNSO_2R_3$, $CONR_3CN$,

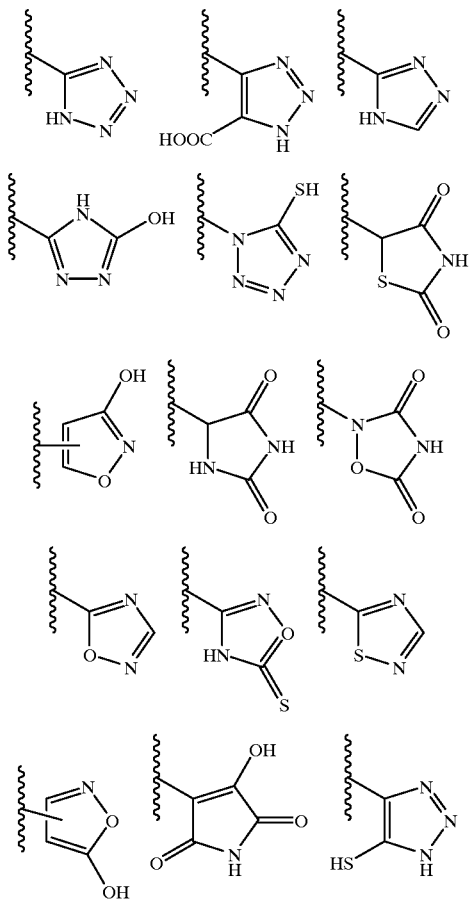

-continued

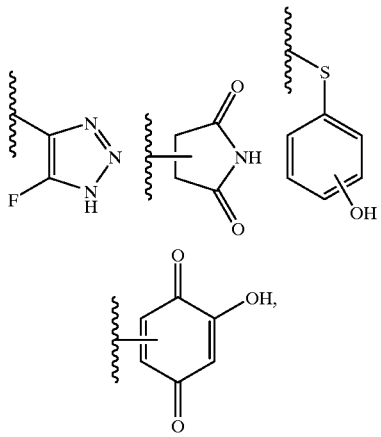

wherein said $R_1$ group is unsubstituted or substituted with one or more substituent(s);

$R_2$ and $R_3$ are independently hydrogen, $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s); and X is O or S.

2. The compound of claim 1, wherein said compound is selected from the group consisting of:

3,3-dimethyl-1-[2-(6-phenylhexanoyl)perhydro-pyridazinyl]pentane-1,2-dione;

3,3-dimethyl-1-[2-(6-(3-pyridyl)hexanoyl)-perhydropyridazinyl]pentane-1,2-dione;

3-phenylpropyl 2-(3,3-dimethyl-2-oxopentanoyl)-perhydropyridazinecarboxylate;

4-phenylbutyl 2-(3,3-dimethyl-2-oxopentanoyl) perhydropyridazinecarboxylate;

5-phenylpentyl 2-(3,3-dimethyl-2-oxopentanoyl)-perhydropyridazinecarboxylate;

4-(3-pyridyl)butyl 2-(3,3-dimethy-2-oxopentanoyl)-perhydropyridazinecarboxylate;

3,3-dimethyl-1-[2-({5-phenyl}pentanoyl)perhydro-pyridazinyl]pentane-1,2-dione; and pharmaceutically acceptable salts, esters and solvates thereof.

3. A pharmaceutical composition comprising:
(i) a compound of formula I

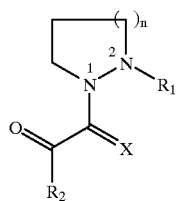

I or a pharmaceutically acceptable salt, ester or solvate thereof, wherein:

n is 2;

$R_1$ is —$CR_3$, —$COOR_3$, —$COR_3$, —$COSR_3$, —$CSSR_3$, —$CSOR_3$, —$SO_3H$, —$SO_2HNR_3$, —CN, —$PO_2(R_3)_2$, —$PO_3(R_3)_2$, —$OR_3$, —$SR_3$, —$NHCOR_3$, —$N(R_3)_2$, —$CON(R_3)_2$, —$CSN(R_3)_2$, —CON(H)—$OR_3$, —$CONHNHSO_2R_3$, —$COHNSO_2R_3$, —$CONR_3CN$,

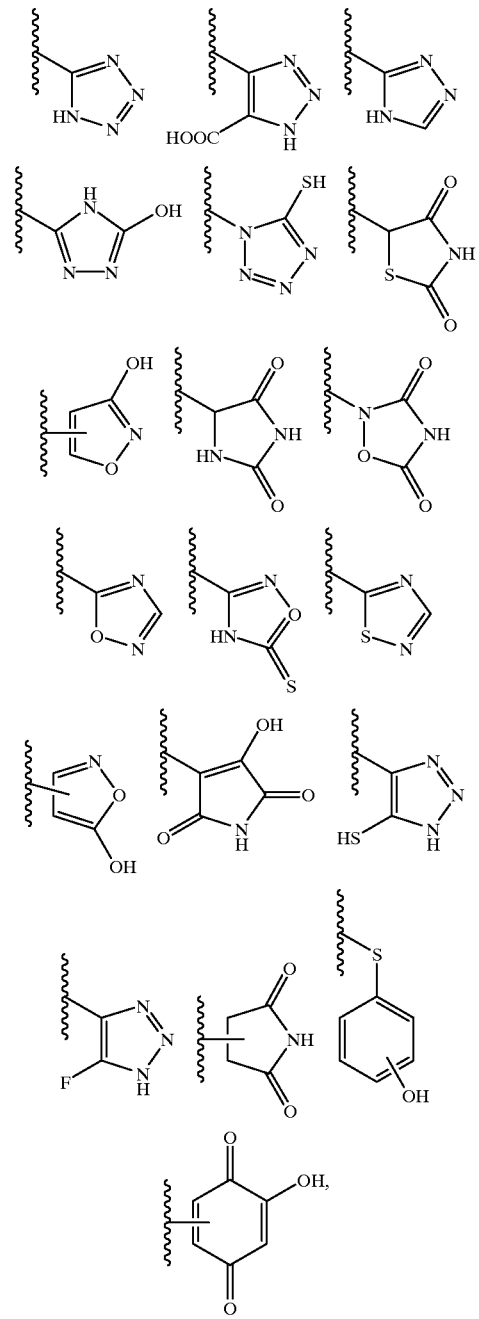

wherein said $R_1$ group is either unsubstituted or substituted within or more substituent(s);

$R_2$ and $R_3$ are independently hydrogen, $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s); and X is O or S; and (ii) a pharmaceutically acceptable carrier.

4. A method for treating a neuronal activity in a mammal, comprising administering to the mammal an effective amount of a compound of formula I,

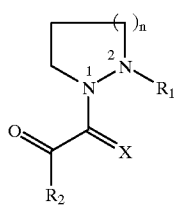

I or a pharmaceutically acceptable salt, ester or solvate thereof, wherein:

n is 2;

R₁ is —CR₃, —COOR₃, —COR₃, —COSR₃, —CSSR₃, —CSOR₃, —SO₃H, —SO₂HNR₃, —CN, —PO₂(R₃)₂, —PO₃(R₃)₂, —OR₃, —SR₃, —NHCOR₃, —N(R₃)₂, —CON(R₃)₂, —CSN (R₃)₂, —CON(H)—OR₃, —CONHNHSO₂R₃, —COHNSO₂R₃, —CONR₃CN,

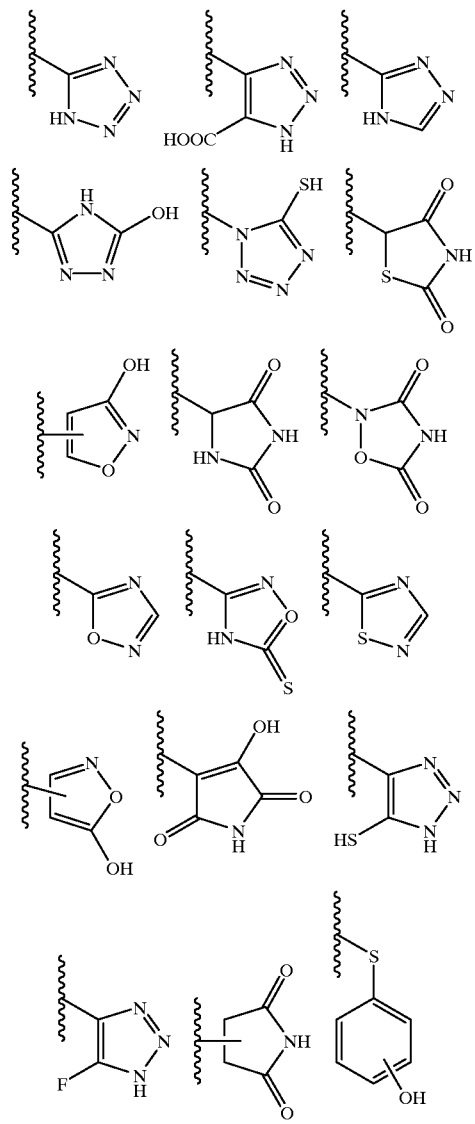

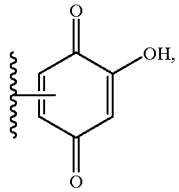

wherein said R₁ group is unsubstituted or substituted with one or more substituent(s);

R₂ and R₃ are independently hydrogen, C₁–C₉ alkyl, C₂–C₉ alkenyl, aryl, heteroaryl, carbocycle or heterocycle, wherein said alkyl, alkenyl, aryl, heteroaryl, carbocycle or heterocycle is unsubstituted or substituted with one or more substituent(s); and X is O or S.

5. The method of claim 4, wherein the neuronal activity is selected from the group consisting of stimulation of damaged neurons, promotion of neuronal regeneration, and treatment of neurological disorder.

6. The method of claim 5, wherein the neurological disorder is selected from the group consisting of peripheral neuropathy caused by physical injury or disease state, traumatic injury to the brain, physical damage to the spinal cord, stroke associated with brain damage, and neurological disorder relating to neurodegeneration.

7. The method of claim 6, wherein the neurological disorder relating to neurodegeneration is selected from the group consisting of Alzheimer's disease, Parkinson's disease, Huntington's disease and amyotrophic lateral sclerosis.

8. A compound of formula II

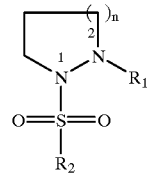

II or a pharmaceutically acceptable salt, ester or solvate thereof, wherein:

n is 2;

R₁ is —CR₃, —COOR₃, —COR₃, —COSR₃, —CSSR₃, —CSOR₃, —SO₃H, —SO₂HNR₃, —CN, —PO₂(R₃)₂, —PO₃ (R₃)₂, —OR₃, —SR₃, —NHCOR₃, —N(R₃)₂, —CSN(R₃)₂, —CON(H)-OR₃, —CONHNHSO₂R₃, —COHNSO₂R₃, —CONR₃CN,

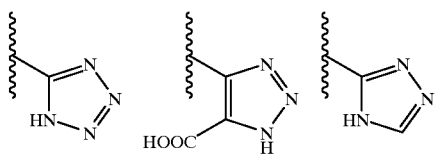

-continued

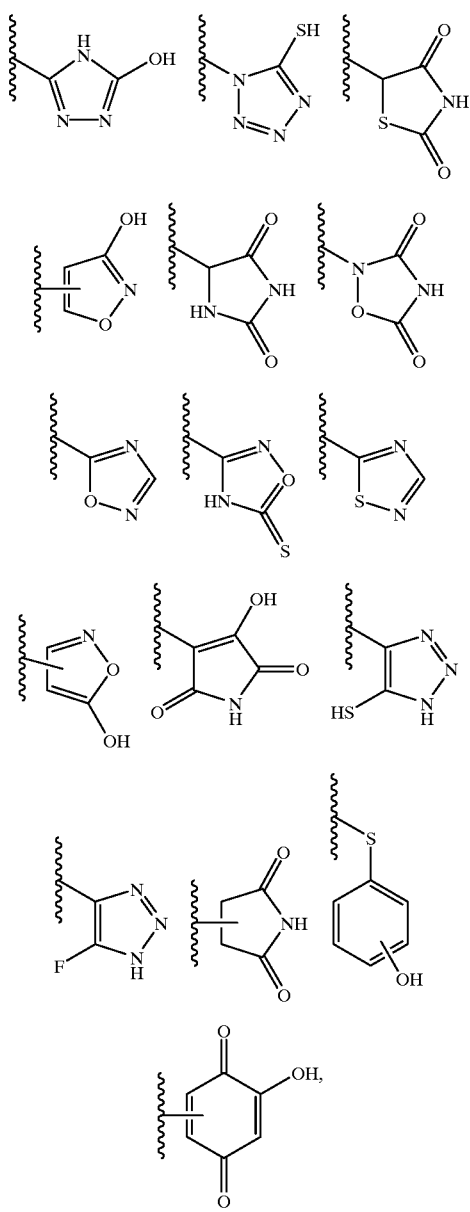

wherein said $R_1$ group is unsubstituted or substituted with one or more substituent(s); and $R_2$ and $R_3$ are independently hydrogen, $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s).

9. The compound of claim 8, which is selected from the group consisting of:

4-phenylbutyl 2-[benzylsulfonyl]perhydropyridazinecarboxylate; and pharmaceutically acceptable salts, esters and solvates thereof.

10. A pharmaceutical composition comprising:

(i) a compound of formula II

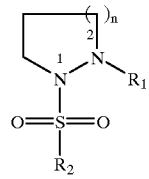

or a pharmaceutically acceptable salt, ester or solvate thereof, wherein:

n is 2;

$R_1$ is —$CR_3$, —$COOR_3$, —$COR_3$, —$COSR_3$, —$CSSR_3$, —$CSOR_3$, —$SO_3H$, —$SO_2HNR_3$, —$CN$, —$PO_2(R_3)_2$, —$PO_3(R_3)_2$, —$OR_3$, —$SR_3$, —$NHCOR_3$, —$N(R_3)_2$, —$CSN(R_3)_2$, —$CON(H)$—$OR_3$, —$OR_3$, —$CONHNHSO_2R_3$, —$COHNSO_2R_3$, —$CONR_3CN$,

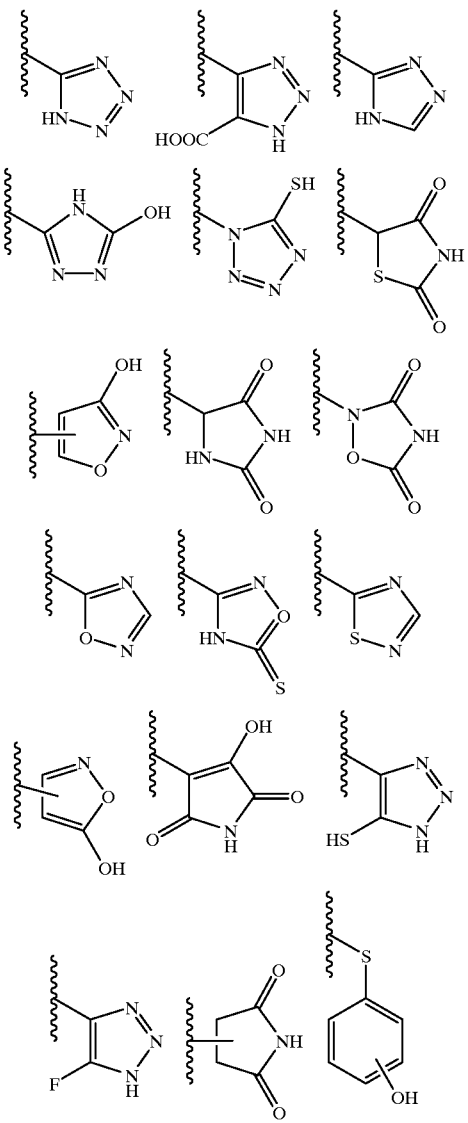

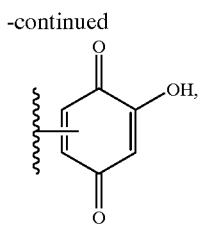

wherein said $R_1$ group is unsubstituted or substituted with one or more substituent(s); and $R_2$ and $R_3$ are independently hydrogen, $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s); and (ii) a pharmaceutically acceptable carrier.

11. A method for treating a neuronal activity in a mammal, comprising administering to the mammal an effective amount of a compound of formula II

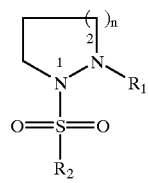

II or a pharmaceutically acceptable salt, ester or solvate thereof, wherein:

n is 2;

$R_1$ is —$CR_3$, —$COOR_3$, —$COR_3$, —$COSR_3$, —$CSSR_3$, —$CSOR_3$, —$SO_3H$, —$SO_2HNR_3$, —CN, —$PO_2(R_3)_2$, —$PO_3(R_3)_2$, —$OR_3$, —$SR_3$, —$NHCOR_3$, —$N(R_3)_2$, —$CSN(R_3)_2$, —CON(H)—$OR_3$, —$CONHNHSO_2R_3$, —$COHNSO_2R_3$, —$CONR_3CN$,

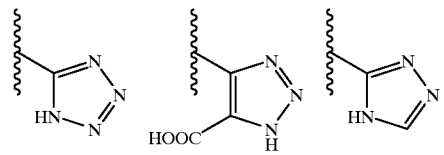

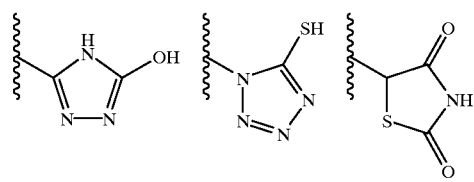

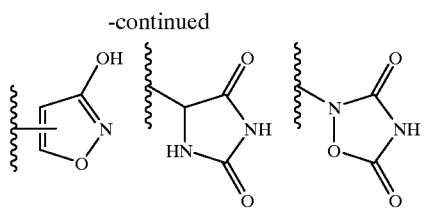

wherein said $R_1$ group is unsubstituted or substituted with one or more substituent(s); and $R_2$ and $R_3$ are independently hydrogen, $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s).

12. The method of claim 11, wherein the neuronal activity is selected from the group consisting of stimulation of damaged neurons, promotion of neuronal regeneration, and treatment of neurological disorder.

13. The method of claim 12, wherein the neurological disorder is selected from the group consisting of peripheral neuropathy caused by physical injury or disease state, traumatic injury to the brain, physical damage to the spinal cord, stroke associated with brain damage, and neurological disorder relating to neurodegeneration.

14. The method of claim 13, wherein the neurological disorder relating to neurodegeneration is selected from the group consisting of Alzheimer's disease, Parkinson's disease, Huntington's disease and amyotrophic lateral sclerosis.

15. A compound of formula III

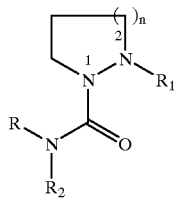

III or a pharmaceutically acceptable salt, ester or solvate thereof, wherein:

n is 2;

$R_1$ is —$CR_3$, —$COOR_3$, —$COR_3$, —$COSR_3$, —$CSSR_3$, —$CSOR_3$, —$SO_3H$, —$SO_2HNR_3$, —CN, —$PO_2(R_3)_2$, —$PO_3(R_3)_2$, —$OR_3$, —$SR_3$, —$NHCOR_3$, —$N(R_3)_2$, —$CON(R_3)_2$, —$CSN(R_3)_2$, —CON(H)—$OR_3$, —$CONHNHSO_2R_3$, —$COHNSO_2R_3$, —$CONR_3CN$,

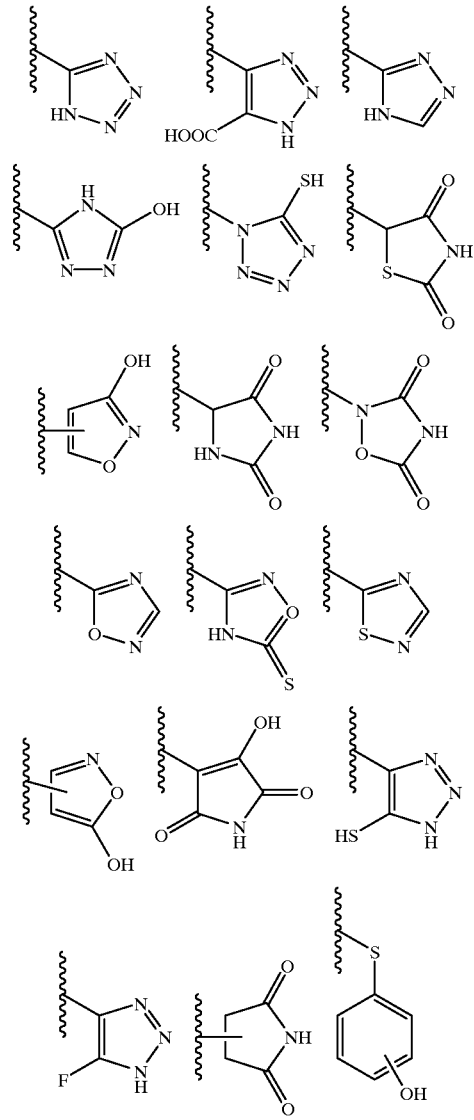

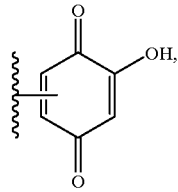

wherein said $R_1$ group is unsubstituted or substituted with one or more substituent(s);

R and $R_2$ are independently $C_1$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s); and $R_3$ is hydrogen $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s).

16. A pharmaceutical composition comprising:

(i) a compound of formula III

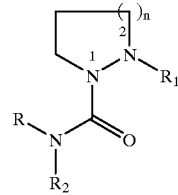

III or a pharmaceutically acceptable salt, ester or solvate thereof, wherein:

n is 2;

$R_1$ is —$CR_3$, —$COOR_3$, —$COR_3$, —$COSR_3$, —$CSSR_3$, —$CSOR_3$, —$SO_3H$, —$SO_2HNR_3$, —CN, —$PO_2(R_3)_2$, —$PO_3(R_3)_2$, —$OR_3$, —$SR_3$, —$NHCOR_3$, —$N(R_3)_2$, —$CON(R_3)_2$, —$CSN(R_3)_2$, —CON(H)—$OR_3$, —$CONHNHSO_2R_3$, —$COHNSO_2R_3$, —$CONR_3CN$,

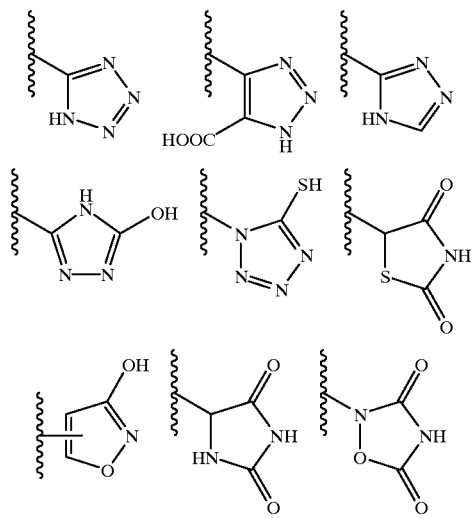

-continued

[chemical structures]

wherein said R₁ group is unsubstituted or substituted with one or more substituent(s);

R and R₂ are independently $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s); and R₃ is hydrogen $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s); and (ii) a pharmaceutically acceptable carrier.

17. A method for treating a neuronal activity in a mammal, comprising administering to the mammal an effective amount of a compound of formula III

III

[chemical structure]

or a pharmaceutically acceptable salt, ester or solvate thereof, wherein:

n is 2;

R₁ is —CR₃, —COOR₃, —COR₃, —COSR₃, —CSSR₃, —CSOR₃, —SO₃H, —SO₂HNR₃, —CN, —PO₂(R₃)₂, —PO₃(R₃)₂, —OR₃, —SR₃, —NHCOR₃, —N(R₃)₂,

—CON(R₃)₂, —CSN(R₃)₂, —CON(H)—OR₃, —CONHNHSO₂R₃, —COHNSO₂R₃, —CONR₃CN,

[chemical structures]

wherein said R₁ group is unsubstituted or substituted with one or more substituent(s);

R and R₂ are independently $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s); and R₃ is hydrogen $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s).

18. The method of claim 17, wherein the neuronal activity is selected from the group consisting of stimulation of damaged neurons, promotion of neuronal regeneration, and treatment of neurological disorder.

19. The method of claim 18, wherein the neurological disorder is selected from the group consisting of peripheral neuropathy caused by physical injury or disease state, traumatic injury to the brain, physical damage to the spinal cord, stroke associated with brain damage, and neurological disorder relating to neurodegeneration.

20. The method of claim 19, wherein the neurological disorder relating to neurodegeneration is selected from the group consisting of Alzheimer's disease, Parkinson's disease, Huntington's disease and amyotrophic lateral sclerosis.

21. A compound of formula IV

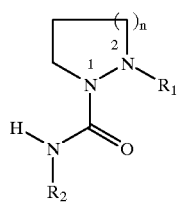

or a pharmaceutically acceptable salt, ester or solvate thereof, wherein:

n is 2;

$R_1$ is —$CR_3$, —$COOR_3$, —$COR_3$, —$COSR_3$, —$CSSR_3$, —$CSOR_3$, —$SO_3H$, —$SO_2HNR_3$, —$CN$, —$PO_2(R_3)_2$, —$PO_3(R_3)_2$, —$OR_3$, —$SR_3$, —$NHCOR_3$, —$N(R_3)_2$, —$CON(R_3)_2$, —$CSN(R_3)_2$, —$CON(H)$—$OR_3$, —$CONHNHSO_2R_3$, —$COHNSO_2R_3$, —$CONR_3CN$,

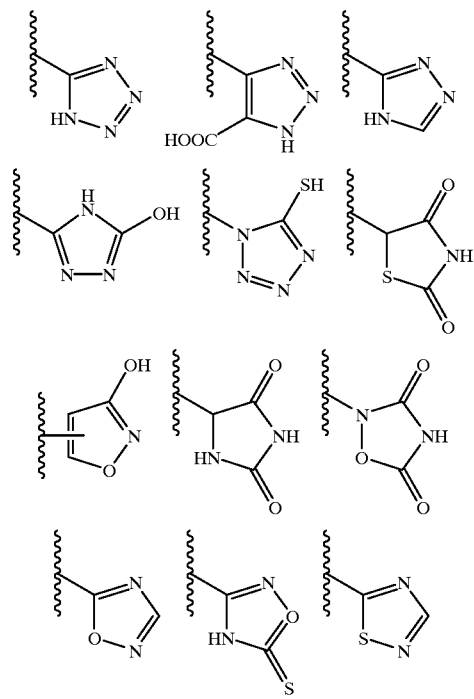

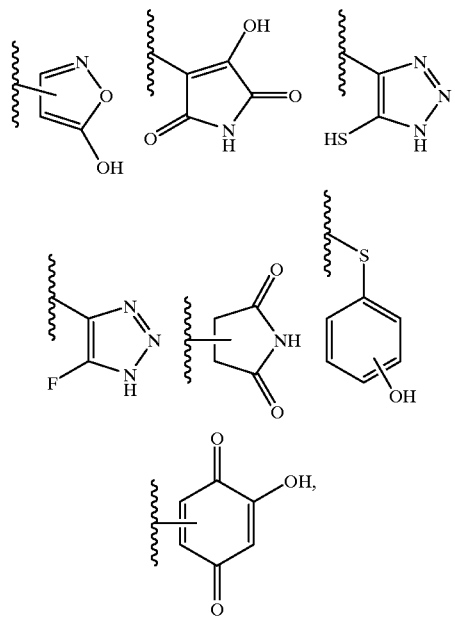

wherein said $R_1$ group is unsubstituted or substituted with one or more substituent(s);

$R_2$ is $C_4$–$C_9$ alkyl, $C_2$–$C_9$ alkenyl, heteroaryl, $C_3$–$C_8$ cycloalkyl, $C_5$–$C_8$ cycloalkenyl, or heterocycle, wherein said alkyl, alkenyl, heteroaryl, cycloalkyl, cycloalkenyl, or heterocycle is unsubstituted; and $R_3$ is hydrogen, $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s).

22. The compound of claim 21, wherein said compound is selected from the group consisting of:

4-phenylbutyl 2-(N-cyclohexylcarbamoyl)perhydropyridazinecarboxylate; and pharmaceutically acceptable salts, esters and solvates thereof.

23. A pharmaceutical composition comprising:
(i) a compound of formula IV

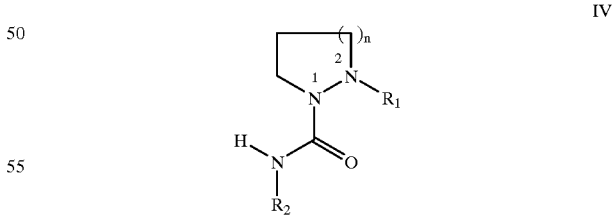

or a pharmaceutically acceptable salt, ester or solvate thereof, wherein:

n is 2;

$R_1$ is —$CR_3$, —$COOR_3$, —$COR_3$, —$COSR_3$, —$CSSR_3$, —$CSOR_3$, —$SO_3H$, —$SO_2HNR_3$, —$CN$, —$PO_2(R_3)_2$, —$PO_3(R_3)_2$, —$OR_3$, —$SR_3$, —$NHCOR_3$, —$N(R_3)_2$, —$CON(R_3)_2$, —$CSN(R_3)_2$, —$CON(H)$—$OR_3$, —$CONHNHSO_2R_3$, —$COHNSO_2R_3$, —$CONR_3CN$,

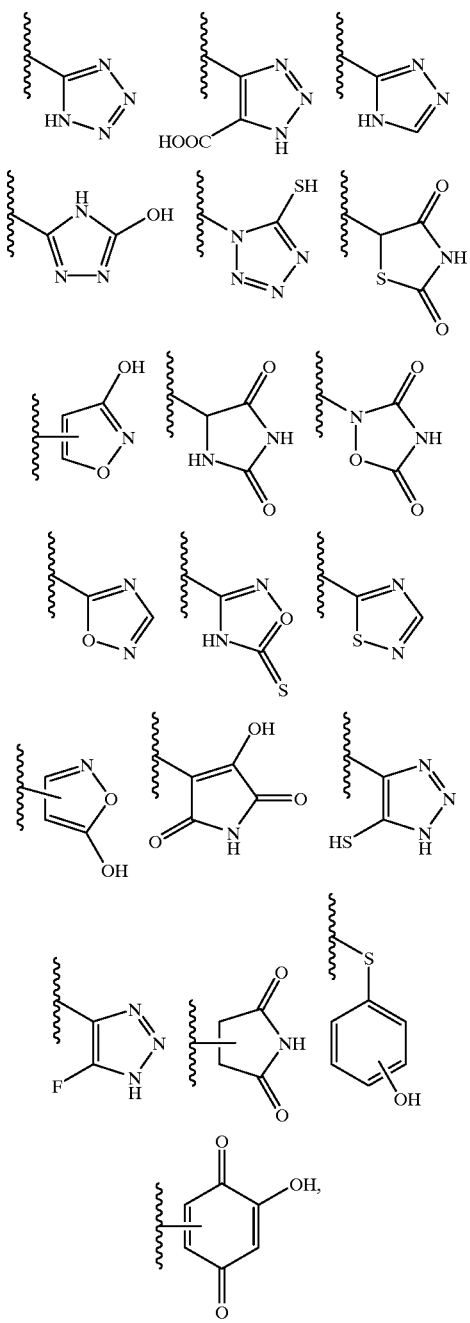

wherein said $R_1$ group is unsubstituted or substituted with one or more substituent(s);

$R_2$ is $C_4$–$C_9$ alkyl, $C_2$–$C_9$ alkenyl, heteroaryl, $C_3$–$C_8$ cycloalkyl, $C_5$–$C_8$ cycloalkenyl, or heterocycle, wherein said alkyl, alkenyl, heteroaryl, cycloalkyl, cycloalkenyl, or heterocycle is unsubstituted; and $R_3$ is hydrogen, $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s); and (ii) a pharmaceutically acceptable carrier.

24. A method for treating a neuronal activity in a mammal, comprising administering to the mammal an effective amount of a compound of formula IV

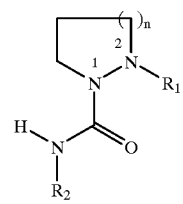

IV or a pharmaceutically acceptable salt, ester or solvate thereof, wherein:

n is 2;

$R_1$ is —$CR_3$, —$COOR_3$, —$COR_3$, —$COSR_3$, —$CSSR_3$, —$CSOR_3$, —$SO_3H$, —$SO_2HNR_3$, —$CN$, —$PO_2(R_3)_2$, —$PO_3(R_3)_2$, —$OR_3$, —$SR_3$, —$NHCOR_3$, —$N(R_3)_2$, —$CON(R_3)_2$, —$CSN(R_3)_2$, —$CON(H)$—$OR_3$, —$CONHNHSO_2R_3$, —$COHNSO_2R_3$, —$CONR_3CN$,

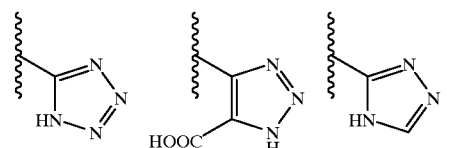

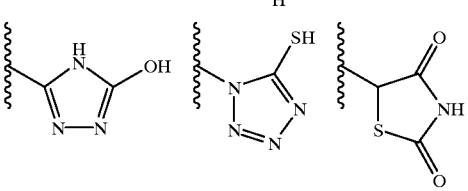

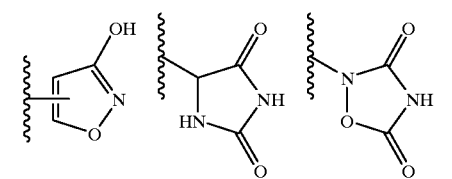

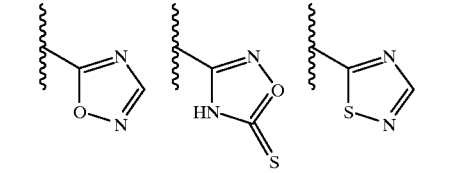

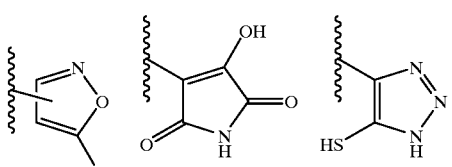

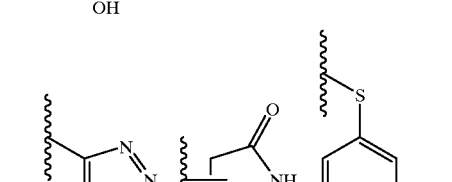

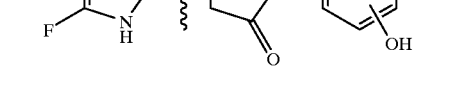

-continued

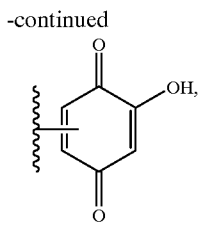

wherein said $R_1$ group is unsubstituted or substituted with one or more substituent(s);

$R_2$ is $C_4$–$C_9$ alkyl, $C_2$–$C_9$ alkenyl, heteroaryl, $C_3$–$C_8$ cycloalkyl, $C_5$–$C_8$ cycloalkenyl, or heterocycle, wherein said alkyl, alkenyl, heteroaryl, cycloalkyl, cycloalkenyl, or heterocycle is unsubstituted; and $R_3$ is hydrogen, $C_1$–$C_9$ alkyl, $C_2$–$C_9$ alkenyl, aryl, heteroaryl, carbocycle or heterocycle, wherein said alkyl, alkenyl, aryl, heteroaryl, carbocycle or heterocycle is unsubstituted or substituted with one or more substituent(s).

25. The method of claim 24, wherein the neuronal activity is selected from the group consisting of stimulation of damaged neurons, promotion of neuronal regeneration, and treatment of neurological disorder.

26. The method of claim 25, wherein the neurological disorder is selected from the group consisting of peripheral neuropathy caused by physical injury or disease state, traumatic injury to the brain, physical damage to the spinal cord, stroke associated with brain damage, and neurological disorder relating to neurodegeneration.

27. The method of claim 26, wherein the neurological disorder relating to neurodegeneration is selected from the group consisting of Alzheimer's disease, Parkinson's disease, Huntington's disease and amyotrophic lateral sclerosis.

* * * * *